(12) United States Patent
Dearden et al.

(10) Patent No.: US 10,449,377 B2
(45) Date of Patent: Oct. 22, 2019

(54) HIGH EFFICIENCY MAGNETIC LINK FOR IMPLANTABLE DEVICES

(71) Applicant: ALFRED E. MANN FOUNDATION FOR SCIENTIFIC RESEARCH, Santa Clarita, CA (US)

(72) Inventors: Brian R. Dearden, Pasadena, CA (US); Glen A. Griffith, Newbury Park, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 4 days.

(21) Appl. No.: 15/817,997

(22) Filed: Nov. 20, 2017

(65) Prior Publication Data
US 2018/0133489 A1    May 17, 2018

Related U.S. Application Data

(63) Continuation of application No. 14/446,291, filed on Jul. 29, 2014, now Pat. No. 9,855,436.
(Continued)

(51) Int. Cl.
*H02J 7/00* (2006.01)
*A61N 1/378* (2006.01)
(Continued)

(52) U.S. Cl.
CPC ....... *A61N 1/3787* (2013.01); *A61N 1/36125* (2013.01); *H02J 7/0042* (2013.01);
(Continued)

(58) Field of Classification Search
CPC ....... Y02E 60/12; H02J 7/0042; H02J 7/0045; H01M 10/46; H01M 10/44
(Continued)

(56) References Cited

U.S. PATENT DOCUMENTS 3,646,940 A   3/1972   Timm et al.
3,942,535 A   3/1976   Schulman et al.
(Continued)

FOREIGN PATENT DOCUMENTS

CN   105263572        1/2016
DE   102010006837 A1  8/2011
(Continued)

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis,The Journal of Urology, Aug. 1995, vol. 154, pp. 504-507.
(Continued)

*Primary Examiner* — Arun C Williams
(74) *Attorney, Agent, or Firm* — Kilpatrick Townsend & Stockton LLP

(57) ABSTRACT

Systems and devices for a high-efficiency magnetic link for implantable devices are disclosed herein. These devices can include a charging coil located in the implantable device and a charging coil located in a charge head of a charger. The charging coils can each include an elongate core and wire windings wrapped around a longitudinal axis of the elongate core. The charging coil of the charge head can be attached to a rotatable mount, which can be used to align the longitudinal axis of the charging coil of the charge head with longitudinal axis of the implantable device such that the axes of the charging coils are parallel.

28 Claims, 12 Drawing Sheets

Related U.S. Application Data

(60) Provisional application No. 61/859,478, filed on Jul. 29, 2013.

(51) Int. Cl.
  *H02J 50/80* (2016.01)
  *H02J 50/10* (2016.01)
  *A61N 1/36* (2006.01)
  *H02J 17/00* (2006.01)
  *H02J 7/02* (2016.01)

(52) U.S. Cl.
  CPC .............. *H02J 7/025* (2013.01); *H02J 17/00* (2013.01); *H02J 50/10* (2016.02); *H02J 50/80* (2016.02); *H02J 7/007* (2013.01); *H02J 7/0052* (2013.01)

(58) Field of Classification Search
  USPC ....................................................... 320/107
  See application file for complete search history.

(56) References Cited

U.S. PATENT DOCUMENTS

| | | | |
|---|---|---|---|
| 4,019,518 | A | 4/1977 | Maurer et al. |
| 4,044,774 | A | 8/1977 | Corbin et al. |
| 4,082,097 | A | 4/1978 | Mann et al. |
| 4,340,062 | A | 7/1982 | Thompson et al. |
| 4,468,723 | A | 8/1984 | Hughes |
| 4,558,702 | A | 12/1985 | Barreras et al. |
| 4,673,867 | A | 6/1987 | Davis |
| 4,744,371 | A | 5/1988 | Harris |
| 5,143,089 | A | 9/1992 | Alt |
| 5,690,693 | A | 11/1997 | Wang et al. |
| 5,702,428 | A | 12/1997 | Tippey et al. |
| 5,702,431 | A | 12/1997 | Wang et al. |
| 5,735,887 | A | 4/1998 | Barreras, Sr. et al. |
| 5,741,316 | A | 4/1998 | Chen et al. |
| 5,755,748 | A | 5/1998 | Borza |
| 5,876,423 | A | 3/1999 | Braun |
| 5,877,472 | A | 3/1999 | Campbell et al. |
| 6,027,456 | A | 2/2000 | Feler et al. |
| 6,035,237 | A | 3/2000 | Schulman et al. |
| 6,055,456 | A | 4/2000 | Gerber |
| 6,057,513 | A | 5/2000 | Ushikoshi et al. |
| 6,067,474 | A | 5/2000 | Schulman et al. |
| 6,076,017 | A | 6/2000 | Taylor et al. |
| 6,164,284 | A | 12/2000 | Schulman et al. |
| 6,172,556 | B1 | 1/2001 | Prentice |
| 6,178,353 | B1 | 1/2001 | Griffith et al. |
| 6,185,452 | B1 | 2/2001 | Schulman et al. |
| 6,191,365 | B1 | 2/2001 | Avellanet |
| 6,208,894 | B1 | 3/2001 | Schulman et al. |
| 6,212,431 | B1 | 4/2001 | Hahn et al. |
| 6,221,513 | B1 | 4/2001 | Lasater |
| 6,246,911 | B1 | 6/2001 | Seligman |
| 6,249,703 | B1 | 6/2001 | Stanton et al. |
| 6,265,789 | B1 | 7/2001 | Honda et al. |
| 6,306,100 | B1 | 10/2001 | Prass |
| 6,313,779 | B1 | 11/2001 | Leung et al. |
| 6,315,721 | B2 | 11/2001 | Schulman et al. |
| 6,324,430 | B1 | 11/2001 | Zarinetchi et al. |
| 6,324,431 | B1 | 11/2001 | Zarinetchi et al. |
| 6,331,744 | B1 | 12/2001 | Chen et al. |
| 6,354,991 | B1 | 3/2002 | Gross et al. |
| 6,360,750 | B1 | 3/2002 | Gerber et al. |
| 6,389,318 | B1 | 5/2002 | Zarinetchi et al. |
| 6,393,325 | B1 | 5/2002 | Mann et al. |
| 6,415,186 | B1 | 7/2002 | Chim et al. |
| 6,427,086 | B1 | 7/2002 | Fischel! et al. |
| 6,438,423 | B1 | 8/2002 | Rezai et al. |
| 6,442,434 | B1 | 8/2002 | Zarinetchi et al. |
| 6,466,817 | B1 | 10/2002 | Kaula et al. |
| 6,505,075 | B1 | 1/2003 | Weiner |
| 6,516,227 | B1 | 2/2003 | Meadows et al. |
| 6,521,350 | B2 | 2/2003 | Fey et al. |
| 6,564,807 | B1 | 5/2003 | Schulman et al. |
| 6,584,355 | B2 | 6/2003 | Slessman |
| 6,600,954 | B2 | 7/2003 | Cohen et al. |
| 6,609,031 | B1 | 8/2003 | Law et al. |
| 6,609,032 | B1 | 8/2003 | Woods et al. |
| 6,652,449 | B1 | 11/2003 | Gross et al. |
| 6,662,051 | B1 | 12/2003 | Eraker et al. |
| 6,701,188 | B2 | 3/2004 | Stroebel et al. |
| 6,721,603 | B2 | 4/2004 | Zabara et al. |
| 6,735,474 | B1 | 5/2004 | Loeb et al. |
| 6,745,077 | B1 | 6/2004 | Griffith et al. |
| 6,809,701 | B2 | 10/2004 | Amundson et al. |
| 6,836,684 | B1 | 12/2004 | Rijkhoff et al. |
| 6,847,849 | B2 | 1/2005 | Mamo et al. |
| 6,864,755 | B2 | 3/2005 | Moore |
| 6,885,894 | B2 | 4/2005 | Slessman |
| 6,892,098 | B2 | 5/2005 | Ayal et al. |
| 6,895,280 | B2 | 5/2005 | Meadows et al. |
| 6,896,651 | B2 | 5/2005 | Gross et al. |
| 6,901,287 | B2 | 5/2005 | Davis et al. |
| 6,941,171 | B2 | 9/2005 | Mann et al. |
| 6,971,393 | B1 | 12/2005 | Mamo et al. |
| 6,986,453 | B2 | 1/2006 | Jiang et al. |
| 6,989,200 | B2 | 1/2006 | Byers et al. |
| 6,990,376 | B2 | 1/2006 | Tanagho et al. |
| 6,999,819 | B2 | 2/2006 | Swoyer et al. |
| 7,051,419 | B2 | 5/2006 | Schrom et al. |
| 7,054,689 | B1 | 5/2006 | Whitehurst et al. |
| 7,069,081 | B2 | 6/2006 | Biggs et al. |
| 7,114,502 | B2 | 10/2006 | Schulman et al. |
| 7,127,298 | B1 | 10/2006 | He et al. |
| 7,142,925 | B1 | 11/2006 | Bhadra et al. |
| 7,146,219 | B2 | 12/2006 | Sieracki et al. |
| 7,151,914 | B2 | 12/2006 | Brewer |
| 7,167,749 | B2 | 1/2007 | Biggs et al. |
| 7,177,690 | B2 | 2/2007 | Woods et al. |
| 7,177,698 | B2 | 2/2007 | Klosterman et al. |
| 7,181,286 | B2 | 2/2007 | Sieracki et al. |
| 7,187,978 | B2 | 3/2007 | Malek et al. |
| 7,191,005 | B2 | 3/2007 | Slessman |
| 7,212,110 | B1 | 5/2007 | Martin et al. |
| 7,225,032 | B2 | 5/2007 | Schmeling et al. |
| 7,231,254 | B2 | 6/2007 | Dilorenzo |
| 7,234,853 | B2 | 6/2007 | Givoletti |
| 7,245,972 | B2 | 7/2007 | Davis |
| 7,286,880 | B2 | 10/2007 | Olson et al. |
| 7,305,268 | B2 | 12/2007 | Gliner et al. |
| 7,317,948 | B1 | 1/2008 | King et al. |
| 7,324,852 | B2 | 1/2008 | Barolat et al. |
| 7,324,853 | B2 | 1/2008 | Ayal et al. |
| 7,328,068 | B2 | 2/2008 | Spinelli et al. |
| 7,330,764 | B2 | 2/2008 | Swover et al. |
| 7,331,499 | B2 | 2/2008 | Jiang et al. |
| 7,359,751 | B1 | 4/2008 | Erickson et al. |
| 7,369,894 | B2 | 5/2008 | Gerber |
| 7,386,348 | B2 | 6/2008 | North et al. |
| 7,387,603 | B2 | 6/2008 | Gross et al. |
| 7,396,265 | B2 | 7/2008 | Darley et al. |
| 7,415,308 | B2 | 8/2008 | Gerber et al. |
| 7,444,181 | B2 | 10/2008 | Shi et al. |
| 7,450,991 | B2 | 11/2008 | Smith et al. |
| 7,460,911 | B2 | 12/2008 | Cosendai et al. |
| 7,463,928 | B2 | 12/2008 | Lee et al. |
| 7,470,236 | B1 | 12/2008 | Kelleher et al. |
| 7,483,752 | B2 | 1/2009 | Von Arx et al. |
| 7,496,404 | B2 | 2/2009 | Meadows et al. |
| 7,513,257 | B2 | 4/2009 | Schulman et al. |
| 7,515,967 | B2 | 4/2009 | Phillips et al. |
| 7,532,936 | B2 | 5/2009 | Erickson et al. |
| 7,539,538 | B2 | 5/2009 | Parramon et al. |
| 7,551,960 | B2 | 6/2009 | ForsberQ et al. |
| 7,555,346 | B1 | 6/2009 | Woods et al. |
| 7,565,203 | B2 | 7/2009 | Greenberg et al. |
| 7,578,819 | B2 | 8/2009 | Bleich et al. |
| 7,580,752 | B2 | 8/2009 | Gerber et al. |
| 7,582,053 | B2 | 9/2009 | Gross et al. |
| 7,599,743 | B2 | 10/2009 | Hassler, Jr. et al. |
| 7,617,002 | B2 | 11/2009 | Goetz |

(56) References Cited

U.S. PATENT DOCUMENTS

| | | | |
|---|---|---|---|
| 7,640,059 B2 | 12/2009 | ForsberQ et al. |
| 7,643,880 B2 | 1/2010 | Tanagho et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,880,337 B2 | 2/2011 | Farkas |
| 7,904,167 B2 | 3/2011 | Klosterman et al. |
| 7,912,547 B2 | 3/2011 | TsenQ et al. |
| 7,912,555 B2 | 3/2011 | Swover et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Passover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,217,535 B2 | 7/2012 | Uchida et al. |
| 8,219,196 B2 | 7/2012 | Torgerson |
| 8,219,202 B2 | 7/2012 | Giftakis et al. |
| 8,219,205 B2 | 7/2012 | TsenQ et al. |
| 8,233,990 B2 | 7/2012 | Goetz |
| 8,255,057 B2 | 8/2012 | Fang et al. |
| 8,310,108 B2 | 11/2012 | Inoue et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | DilmaQhanian et al. |
| 8,494,625 B2 | 7/2013 | HarQrove |
| 8,515,545 B2 | 8/2013 | Trier |
| 8,538,530 B1 | 9/2013 | Orinski |
| 8,543,223 B2 | 9/2013 | Saae et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 9,205,273 B2 | 12/2015 | Dearden et al. |
| 2002/0116042 A1 | 8/2002 | Boling |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2005/0140482 A1 | 6/2005 | Cheng et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2006/0247737 A1* | 11/2006 | Olson ............... A61N 1/08 607/61 |
| 2006/0253173 A1 | 11/2006 | Tsenq et al. |
| 2007/0060968 A1 | 3/2007 | Strother et al. |
| 2007/0060980 A1 | 3/2007 | Strother et al. |
| 2007/0073357 A1 | 3/2007 | Rooney et al. |
| 2007/0185546 A1 | 8/2007 | Tsenq et al. |
| 2007/0265675 A1 | 11/2007 | Lund et al. |
| 2007/0293914 A1 | 12/2007 | Woods et al. |
| 2008/0011800 A1 | 1/2008 | Vandevere et al. |
| 2008/0132961 A1 | 6/2008 | Jaax et al. |
| 2008/0172109 A1 | 7/2008 | Rahman et al. |
| 2008/0183236 A1 | 7/2008 | Gerber |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0227829 A1 | 9/2009 | Burnett et al. |
| 2009/0259273 A1 | 10/2009 | Figueiredo et al. |
| 2010/0076254 A1 | 3/2010 | Jimenez et al. |
| 2010/0076516 A1 | 3/2010 | Padiy et al. |
| 2010/0076534 A1 | 3/2010 | Mock |
| 2010/0256710 A1 | 10/2010 | Dinsmoor et al. |
| 2010/0274319 A1 | 10/2010 | Meskens |
| 2011/0004269 A1 | 1/2011 | Strother et al. |
| 2011/0009924 A1 | 1/2011 | Meskens |
| 2011/0093045 A1 | 4/2011 | Moffitt |
| 2011/0152959 A1 | 6/2011 | Sherwood et al. |
| 2011/0160799 A1 | 6/2011 | Mishra et al. |
| 2011/0193688 A1 | 8/2011 | Forsell |
| 2011/0234155 A1 | 9/2011 | Chen et al. |
| 2011/0270269 A1 | 11/2011 | Swoyer et al. |
| 2011/0278948 A1 | 11/2011 | Forsell |
| 2011/0282416 A1 | 11/2011 | Hamann et al. |
| 2011/0301667 A1 | 12/2011 | Olson et al. |
| 2012/0012630 A1 | 1/2012 | Lui et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |

(56) References Cited

U.S. PATENT DOCUMENTS

| | | |
|---|---|---|
| 2012/0119698 A1 | 5/2012 | Karalis et al. |
| 2012/0123505 A1 | 5/2012 | Kothandaraman |
| 2012/0130448 A1 | 5/2012 | Woods et al. |
| 2012/0150259 A1 | 6/2012 | Meskens |
| 2012/0161540 A1* | 6/2012 | Moon ................. H04B 5/0012 307/104 |
| 2012/0245649 A1 | 9/2012 | Bohori et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2012/0283800 A1 | 11/2012 | Perryman et al. |
| 2013/0006330 A1 | 1/2013 | Wilder et al. |
| 2013/0006331 A1 | 1/2013 | Weisqarber et al. |
| 2013/0023958 A1 | 1/2013 | Fell |
| 2013/0063084 A1 | 3/2013 | Tilvis et al. |
| 2013/0096651 A1 | 4/2013 | Ozawa |
| 2013/0096653 A1 | 4/2013 | Winstrom |
| 2013/0127404 A1 | 5/2013 | Maenpaa |
| 2013/0150925 A1 | 6/2013 | Vamos et al. |
| 2013/0184785 A1 | 7/2013 | Aqhassian |
| 2013/0187478 A1 | 7/2013 | Bae et al. |
| 2013/0197607 A1 | 8/2013 | Wilder et al. |
| 2013/0197608 A1 | 8/2013 | Eiaer |
| 2013/0207863 A1 | 8/2013 | Joshi |
| 2013/0211479 A1 | 8/2013 | Olson et al. |
| 2013/0218228 A1 | 8/2013 | Goossen |
| 2013/0241304 A1 | 9/2013 | Bae |
| 2013/0241306 A1 | 9/2013 | Aber et al. |
| 2013/0303942 A1 | 11/2013 | Damaser et al. |
| 2013/0331909 A1 | 12/2013 | Gerber |
| 2014/0222112 A1 | 8/2014 | Fell |
| 2014/0237806 A1 | 8/2014 | Smith et al. |
| 2015/0028798 A1 | 1/2015 | Dearden et al. |
| 2015/0127069 A1 | 5/2015 | Dearden et al. |
| 2015/0214604 A1 | 7/2015 | Zhao et al. |

FOREIGN PATENT DOCUMENTS

| | | |
|---|---|---|
| EP | 1680182 | 7/2006 |
| EP | 1904153 | 4/2008 |
| EP | 2243509 | 10/2010 |
| EP | 3027271 | 6/2016 |
| JP | 2003/047179 A | 2/2003 |
| JP | 2004/103465 A | 4/2004 |
| JP | 2005/525705 A | 8/2005 |
| JP | 2013121258 A | 6/2013 |
| JP | 2016//528974 | 9/2016 |
| WO | 96/40367 A1 | 5/1996 |
| WO | 98/09588 A1 | 9/1997 |
| WO | 99/06108 A1 | 7/1998 |
| WO | 2000/056677 A1 | 3/2000 |
| WO | 01/37926 A1 | 11/2000 |
| WO | 2000/066221 A1 | 11/2000 |
| WO | 0066221 | 11/2000 |
| WO | 02/094139 A1 | 9/2001 |
| WO | 2002/003408 A2 | 1/2002 |
| WO | 03/022359 A1 | 9/2002 |
| WO | 2004/022130 A3 | 9/2003 |
| WO | 2005/037364 A1 | 9/2004 |
| WO | 2005/037365 A1 | 9/2004 |
| WO | 2005/037370 A1 | 9/2004 |
| WO | 2005/039698 A1 | 9/2004 |
| WO | 2004/103465 | 12/2004 |
| WO | 2007/015599 A1 | 7/2006 |
| WO | 2007/081714 A1 | 1/2007 |
| WO | 2007/136657 A2 | 5/2007 |
| WO | 2008/021524 | 2/2008 |
| WO | 2008/151059 A2 | 5/2008 |
| WO | 2008/038202 A2 | 9/2008 |
| WO | 2009/055856 A1 | 10/2008 |
| WO | 2009/134471 A1 | 1/2009 |
| WO | 2009/051539 | 4/2009 |
| WO | 2009/091267 A2 | 7/2009 |
| WO | 2010/042055 A1 | 10/2009 |
| WO | 2010/042056 | 4/2010 |
| WO | 2010/042057 | 4/2010 |
| WO | 2011/090736 A2 | 12/2010 |
| WO | 2011/119352 | 3/2011 |
| WO | 2011/059565 | 5/2011 |
| WO | 2012/044103 | 9/2011 |
| WO | 2012/067971 | 11/2011 |
| WO | 2012/103519 | 1/2012 |
| WO | 2012/129061 | 3/2012 |
| WO | 2013-109605 | 1/2013 |
| WO | 2013/072553 | 5/2013 |
| WO | 2013/141884 | 9/2013 |
| WO | 2015/017474 | 2/2015 |

OTHER PUBLICATIONS

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Tanagho, E., et al., Bladder Pacemaker: Scientific Basis and Clinical Future, Urology, Dec. 1982, vol. 20, No. 6, pp. 614-619.

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994 (Jan. 1, 1994), pp. 148-152.

Gundason, G., "A low-power ASK demodulator for Inductively coupled implantable electronics", Solid-State Circuits Conference, 2000, Esscirc ''00, Proceedings of the 26rd European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, (Mar. 1, 2005), pp. 763-771.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006 (Dec. 1, 2006), pp. 696-699.

\* cited by examiner

HIGH EFFICIENCY MAGNETIC LINK FOR IMPLANTABLE DEVICES

CROSS-REFERENCES TO RELATED APPLICATIONS

This application is a continuation of U.S. application Ser. No. 14/446,291, entitled "HIGH EFFICIENCY MAGNETIC LINK FOR IMPLANTABLE DEVICES," and filed on Jul. 29, 2014, which claims the benefit of U.S. Provisional Application No. 61/859,478, entitled "HIGH EFFICIENCY MAGNETIC LINK FOR IMPLANTABLE DEVICES," and filed on Jul. 29, 2013, the entirety of each which are hereby incorporated by reference herein.

BACKGROUND OF THE INVENTION

The prevalence of use of medical devices in treating ailments is increasing with time. In many instances, and as these medical devices are made smaller, these medical devices are frequently implanted within a patient. While the desirability of implantable devices is increasing as the size of the devices has decreased, the implantation process still frequently requires complicated surgery which can expose the patient to significant risks and protracted recovery times. In light of this, further methods, systems, and devices are desired to increase the ease of use of implantable and/or implanted medical devices.

BRIEF SUMMARY OF THE INVENTION

One aspect of the present disclosure relates to a method of charging an implantable device. The method includes positioning a charging head including a transmitting coil attached to a rotatable mount proximate to an implantable device including a receiving coil, determining a first orientation of the transmitting coil with respect to the receiving coil, and rotating the rotatable mount and the thereto attached transmitting coil until the transmitting coil has a second orientation with respect to the receiving coil.

In some embodiments, the transmitting coil has a longitudinal axis and at least one wire wrapped around the longitudinal axis. In some embodiments, the receiving coil has a longitudinal axis and at least one wire wrapped around the longitudinal axis.

In some embodiments, determining the first orientation of the transmitting coil with respect to the receiving coil includes determining an angle between the longitudinal axis of the transmitting coil with respect to the longitudinal axis of the receiving coil. In some embodiments, the angle between the longitudinal axis of the transmitting coil is non-parallel with the longitudinal axis of the receiving coil in the first orientation. In some embodiments, an angle between the longitudinal axis of the transmitting coil and the longitudinal axis of the receiving coil in the second orientation is less than the angle between the longitudinal axis of the transmitting coil and the longitudinal axis of the receiving coil in the first orientation. In some embodiments, the charging efficiency in the first orientation is less than the charging efficiency in the second orientation.

In some embodiments, rotating the rotatable mount and the thereto attached transmitting coil until the transmitting coil has a second orientation with respect to the receiving coil includes determining when an angle between the longitudinal axis of the transmitting coil and the longitudinal axis of the charging coil is minimized. In some embodiments, the second orientation is reached when the angle between the longitudinal axis of the transmitting coil and the longitudinal axis of the charging coil is minimized.

One aspect of the present disclosure relates to an implantable device. The implantable device includes a processor that can control the operation of the implantable device and can generate a plurality of electrical impulses for stimulating a peripheral nerve, a lead that can be placed proximate to a peripheral nerve, an energy storage device that can store energy, and a charging coil having an elongate core having a first end, and second end, and a longitudinal axis extending therebetween, and a wire wrapped in a plurality of coils around the elongate core and the longitudinal axis of the elongate core.

In some embodiments, the wire can be litz wire. In some embodiments, the elongate core can be made of a soft ferrite material. In some embodiments, the charging coil has a Q factor of at least 70, and in some embodiments, the charging coil has a Q factor of at least 80. In some embodiments, the charging coil further includes a capacitor electrically connected to the wire, which capacitor can be a high Q COG capacitor. In some embodiments, the capacitor is located on the charging coil, and in some embodiments, the capacitor is located proximate to the charging coil. In some embodiments, the capacitor is positioned so as to create a high Q tank circuit.

One aspect of the present disclosure relates to a charging head. The charging head includes a contact surface, a rotatable mount positioned a distance from the contact surface and rotatable with respect to the contact surface, and a charging coil attached to the rotatable mount.

In some embodiments, the charging coil includes an elongate core having a first end, and a second end, and a longitudinal axis extending therebetween, and a wire wrapped in a plurality of coils around the elongate core and the longitudinal axis of the elongate core. In some embodiments, the elongate core includes a first foot located at the first end and a second foot located at the second end.

In some embodiments, the first and second feet extend towards the contact surface. In some embodiments, the contact surface can be a track that can receive the first and second feet and to allow the rotation of the rotatable mount and the thereto attached charging coil. In some embodiments, the charging coil can rotate at least 180 degrees.

In some embodiments, the wire can be litz wire. In some embodiments, the elongate core can be a soft ferrite material. In some embodiments, the charging coil has a Q factor of at least 50, and in some embodiments, the charging coil has a Q factor of at least 100.

One aspect of the present disclosure relates to a charging system. The charging system includes an implantable device having a receiving coil. In some embodiments, the receiving coil can have an elongate core having a first end, a second end, and a longitudinal axis extending therebetween, and a wire wrapped in a plurality of coils around the elongate core and the longitudinal axis of the elongate core. The charging system can include a charging head having a transmitting coil. In some embodiments, the transmitting coil can include an elongate core having a first end, a second end, and a longitudinal axis extending therebetween, and a wire wrapped in a plurality of coils around the elongate core and the longitudinal axis of the elongate core.

In some embodiments, the receiving coil can be a capacitor electrically connected to the wire of the receiving coil. In some embodiments, the charging head can include a rotatable mount. In some embodiments, the transmitting coil is attached to the rotatable mount. In some embodiments, the rotatable mount is rotatable between a first position and a second position. In some embodiments, the rotatable mount is lockable in the first position and in the second position.

In some embodiments, the charging system can include circuitry that can detect an angular position of the receiving coil with respect to the transmitting coil. In some embodiments, the circuitry that can detect an angular position of the receiving coil with respect to the transmitting coil are in the charging head.

One aspect of the present disclosure relates to a method of charging an implantable device. The method includes positioning an external charger on an outer surface of a person's body proximate an implanted electrical pulse generator, the external charger including a housing and charging coil, the charging coil supported inside the housing such that the charging coil is rotatable inside of the housing, the implanted electrical pulse generator including a charging coil, fixing the position of the external charger on the outer surface of the person's body, and while the external charger is fixed on the outer surface of the person's body, rotating the charging coil of the external charger to change an orientation of the charging coil of the external charger relative to the charging coil of the implanted electrical pulse generator.

In some embodiments, the implanted electrical pulse generator further can be at least one electrode implanted proximate a peripheral nerve of the person.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

Figure 1:
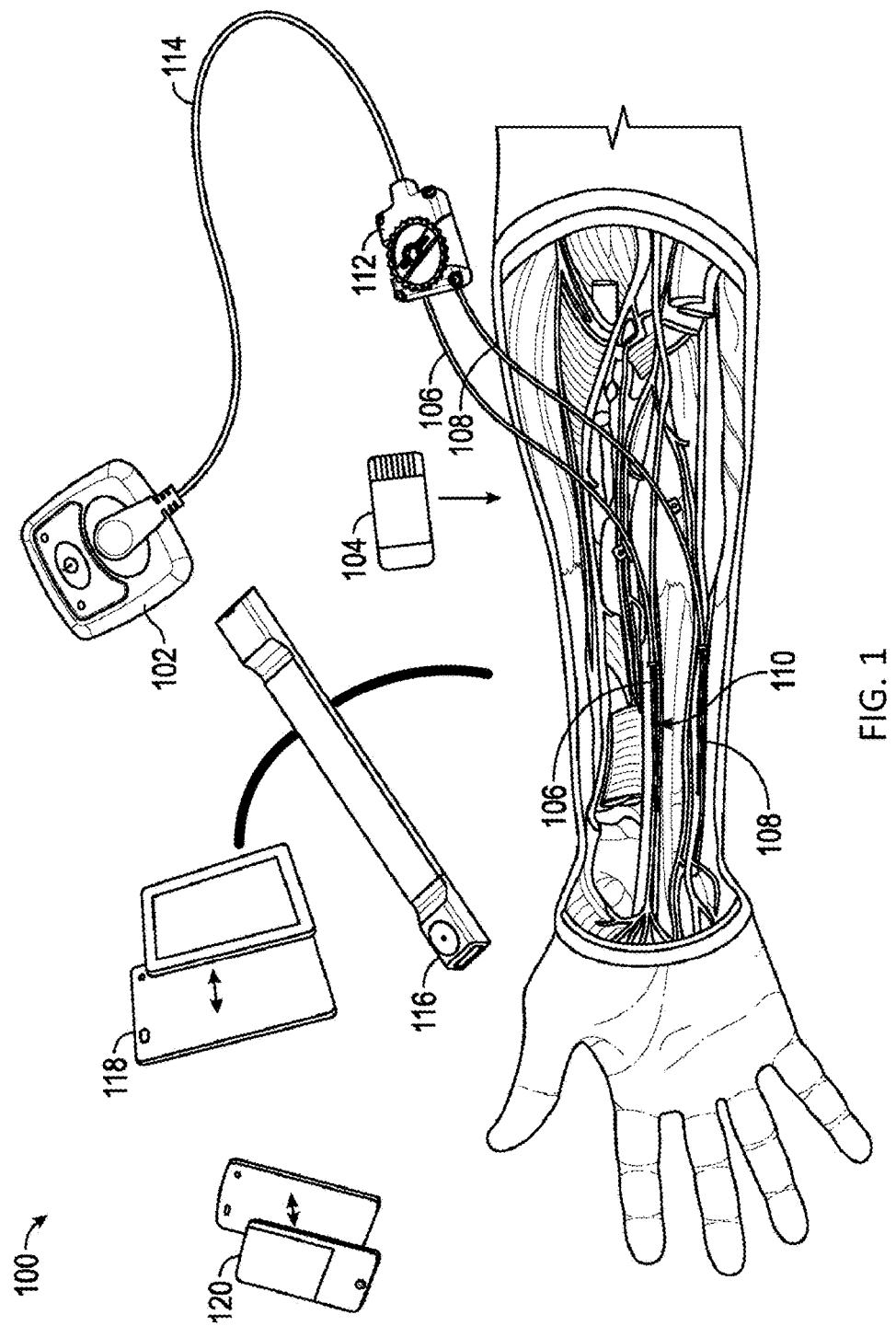
FIG. 1 is a schematic illustration of one embodiment of an implantable neurostimulation system.

In the appended figures, similar components and/or features may have the same reference label. Where the reference label is used in the specification, the description is applicable to any one of the similar components having the same reference label.

DETAILED DESCRIPTION OF THE INVENTION

A significant percentage of the Western (EU and US) population is affected by Neuropathic pain (chronic intractable pain due to nerve damage). In many people, this pain is severe. There are thousands of patients that have chronic intractable pain involving a nerve. Neuropathic pain can be very difficult to treat with only half of patients achieving partial relief. Thus, determining the best treatment for individual patients remains challenging. Conventional treatments include certain antidepressants, anti-epileptic drugs and opioids. However, side effects from these drugs can be detrimental. In some of these cases, electrical stimulation can provide effective treatment of this pain without the drug-related side effects.

A spinal cord stimulator is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. Early SCS trials were based on the Gate Control Theory, which posits that pain is transmitted by two kinds of afferent nerve fibers. One is the larger myelinated A$\delta$ fiber, which carries quick, intense-pain messages. The other is the smaller, unmyelinated "C" fiber, which transmits throbbing, chronic pain messages. A third type of nerve fiber, called A$\beta$, is "non-nociceptive," meaning it does not transmit pain stimuli. The gate control theory asserts that signals transmitted by the A$\delta$ and C pain fibers can be thwarted by the activation/stimulation of the non-nociceptive A$\beta$ fibers and thus inhibit an individual's perception of pain. Thus, neurostimulation provides pain relief by blocking the pain messages before they reach the brain.

SCS is often used in the treatment of failed back surgery syndrome, a chronic pain syndrome that has refractory pain due to ischemia. SCS complications have been reported in a large portion, possibly 30% to 40%, of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: including lead extension connection issues, lead breakage, lead migration and infection.

Peripheral neuropathy, another condition that can be treated with electrical stimulation, may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). As FDA approved PNS devices have not been commercially available in the US market, Standard spinal cord stimulator (SCS) devices are often used off label by pain physicians to treat this condition. A significant portion of SCS devices that have been sold may have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdomen or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates being far too high within the first few years of implantation. Many or even most complications result in replacement surgery and even multiple replacement surgeries in some cases.

One embodiment of an implantable neurostimulation system 100 is shown in FIG. 1, which implantable neurostimulation system 100 can be, for example, a peripherally-implantable neurostimulation system 100. In some embodiments, the implantable neurostimulation system 100 can be used in treating patients with, for example, chronic, severe, refractory neuropathic pain originating from peripheral nerves. In some embodiments, the implantable neurostimulation system 100 can be used to either stimulate a target peripheral nerve or the posterior epidural space of the spine.

The implantable neurostimulation system 100 can include one or several pulse generators. The pulse generators can comprise a variety of shapes and sizes, and can be made from a variety of materials. In some embodiments, the one or several pulse generators can generate one or several non-ablative electrical pulses that are delivered to a nerve to control pain. In some embodiments, these pulses can have a pulse amplitude of between 0-1,000 mA, 0-100 mA, 0-50 mA, 0-25 mA, and/or any other or intermediate range of amplitudes. One or more of the pulse generators can include a processor and/or memory. In some embodiments, the processor can provide instructions to and receive information from the other components of the implantable neurostimulation system 100. The processor can act according to stored instructions, which stored instructions can be located in memory, associated with the processor, and/or in other components of the implantable neurostimulation system 100. The processor can, in accordance with stored instructions, make decisions. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In some embodiments, the memory of one or both of the pulse generators can be the storage medium containing the stored instructions. The memory may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory may be implemented within the processor or external to the processor. In some embodiments, the memory can be any type of long term, short term, volatile, nonvolatile, or other storage medium and is not to be limited to any particular type of memory or number of memories, or type of media upon which memory is stored. In some embodiments, the memory can include, for example, one or both of volatile and nonvolatile memory. In one specific embodiment, the memory can include a volatile portion such as RAM memory, and a nonvolatile portion such as flash memory.

In some embodiments, one of the pulse generators can be an external pulse generator 102 or an implantable pulse generator 104. The external pulse generator 102 can be used to evaluate the suitability of a patient for treatment with the implantable neurostimulation system 100 and/or for implantation of an implantable pulse generator 104.

In some embodiments, one of the pulse generators can be the implantable pulse generator 104, which can be sized and shaped, and made of material to allow implantation of the implantable pulse generator 104 inside of a body. In some embodiments, the implantable pulse generator 104 can be sized and shaped so as to allow placement of the implantable pulse generator 104 at any desired location in a body, and in some embodiments, placed proximate to a peripheral nerve such that leads (discussed below) are not tunneled across joints and/or such that extension cables are not needed.

The implantable pulse generator 104 can include one or several energy storage features. In some embodiments, these features can be configured to store energy, such as, for example, electric energy, that can be used in the operation of the implantable pulse generator 104. These energy storage features can include, for example, one or several batteries, including rechargeable batteries, one or several capacitors, one or several fuel cells, or the like.

In some embodiments, the electrical pulses generated by the pulse generator can be delivered to one or several nerves 110 and/or to tissue proximate to one or several nerves 110 via one or several leads. The leads can include conductive portions, such as electrodes or contact portions of electrodes, and non-conductive portions. The leads can have a variety of shapes, can be a variety of sizes, and can be made from a variety of materials, which size, shape, and materials can be dictated by the application or other factors. In some embodiments, the leads can be implanted proximate to a peripheral nerve. In one embodiment, both the implantable pulse generator 104 and the leads can be implanted in a peripheral portion of the patient's body, and can be configured to deliver one or several electrical pulses to the peripheral nerve.

In some embodiments, the leads can include an anodic lead 106 and/or a cathodic lead 108. In some embodiments, the anodic lead 106 and the cathodic lead 108 can be identical leads, but can receive pulses of different polarity from the pulse generator.

In some embodiments, the leads can connect directly to the pulse generator, and in some embodiments, the leads can be connected to the pulse generator via a connector 112 and a connector cable 114. The connector 112 can comprise any device that is able to electrically connect the leads to the connector cable 114. Likewise, the connector cable can be any device capable of transmitting distinct electrical pulses to the anodic lead 106 and the cathodic lead 108.

In some embodiments, the implantable neurostimulation system 100 can include a charger 116 that can be configured to recharge the implantable pulse generator 104 when the implantable pulse generator 104 is implanted within a body. The charger 116 can comprise a variety of shapes, sizes, and features, and can be made from a variety of materials. Like the pulse generators 102, 104, the charger 116 can include a processor and/or memory having similar characteristics to those discussed above. In some embodiments, the charger 116 can recharge the implantable pulse generator 104 via an inductive coupling.

In some embodiments, one or several properties of the electrical pulses can be controlled via a controller. In some embodiments, these properties can include, for example, the frequency, strength, pattern, duration, or other aspects of the timing and magnitude of the electrical pulses. In one embodiment, these properties can include, for example, a voltage, a current, or the like. In one embodiment, a first electrical pulse can have a first property and a second electrical pulse can have a second property. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 1, the implantable neurostimulation system 100 includes a controller that is a clinician programmer 118. The clinician programmer 118 can be used to create one or several pulse programs, plans, or patterns and/or to select one or several of the created pulse programs, plans, or patterns. In some embodiments, the clinician programmer 118 can be used to program the operation of the pulse generators including, for example, one or both of the external pulse generator 102 and the implantable pulse generator 104. The clinician programmer 118 can comprise a computing device that can wiredly and/or wirelessly communicate with the pulse generators. In some embodiments, the clinician programmer 118 can be further configured to receive information from the pulse generators indicative of the operation and/or effectiveness of the pulse generators and the leads.

In some embodiments, the controller of the implantable neurostimulation system 100 can include a patient remote 120. The patient remote 120 can comprise a computing device that can communicate with the pulse generators via a wired or wireless connection. The patient remote 120 can be used to program the pulse generator, and in some embodiments, the patient remote 120 can include one or several pulse generation programs, plans, or patterns created by the clinician programmer 118. In some embodiments, the patient remote 120 can be used to select one or several of the pre-existing pulse generation programs, plans, or patterns and to select, for example, the duration of the selected one of the one or several pulse generation programs, plans, or patterns.

Advantageously, the above outlined components of the implantable neurostimulation system 100 can be used to control and provide the generation of electrical pulses to mitigate patient pain.

Figure 2:
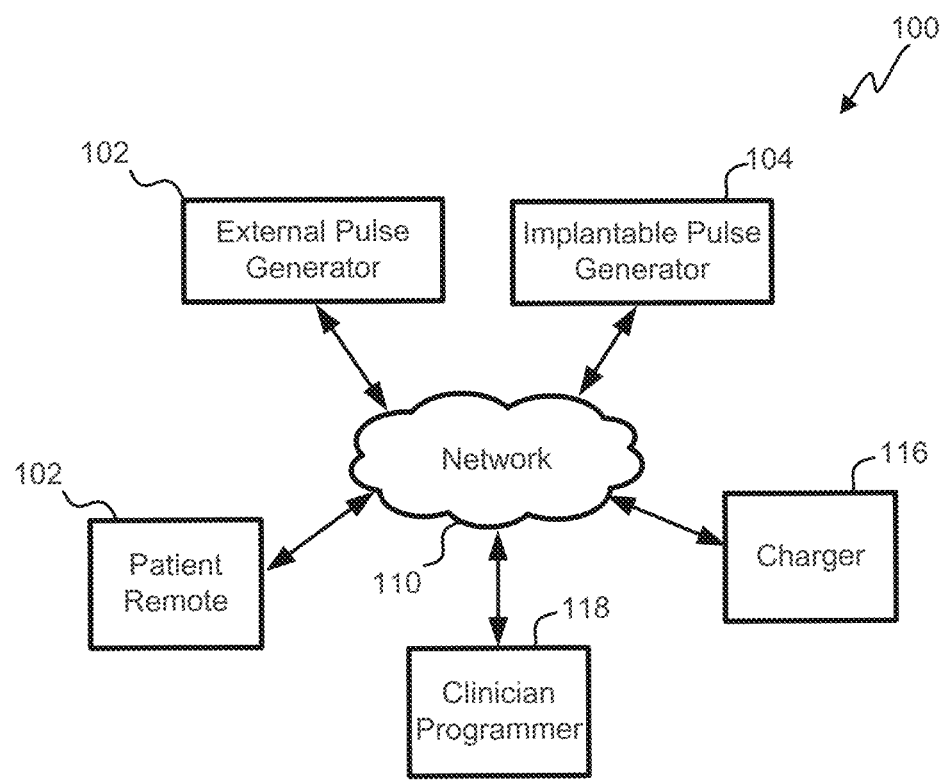
FIG. 2 is a schematic illustration of one embodiment of interconnectivity of the implantable neurostimulation system.

With reference now to FIG. 2, a schematic illustration of one embodiment of interconnectivity of the implantable neurostimulation system 100 is shown. As seen in FIG. 2, several of the components of the implantable neurostimulation system 100 are interconnected via network 110. In some embodiments, the network 110 allows communication between the components of the implantable neurostimulation system 100. The network 110 can be, for example, a local area network (LAN), a wide area network (WAN), a wired network, a custom network, wireless network, a telephone network such as, for example, a cellphone network, the Internet, the World Wide Web, or any other desired network or combinations of different networks. In some embodiments, the network 110 can use any desired communication and/or network protocols. The network 110 can include any communicative interconnection between two or more components of the implantable neurostimulation system 100. In one embodiment, the communications between the devices of the implantable neurostimulation system 100 can be according to any communication protocol including, for example those covered by Near Field Communication (NFC), Bluetooth, or the like. In some embodiments, different components of the system may utilize different communication networks and/or protocols.

Figure 3:
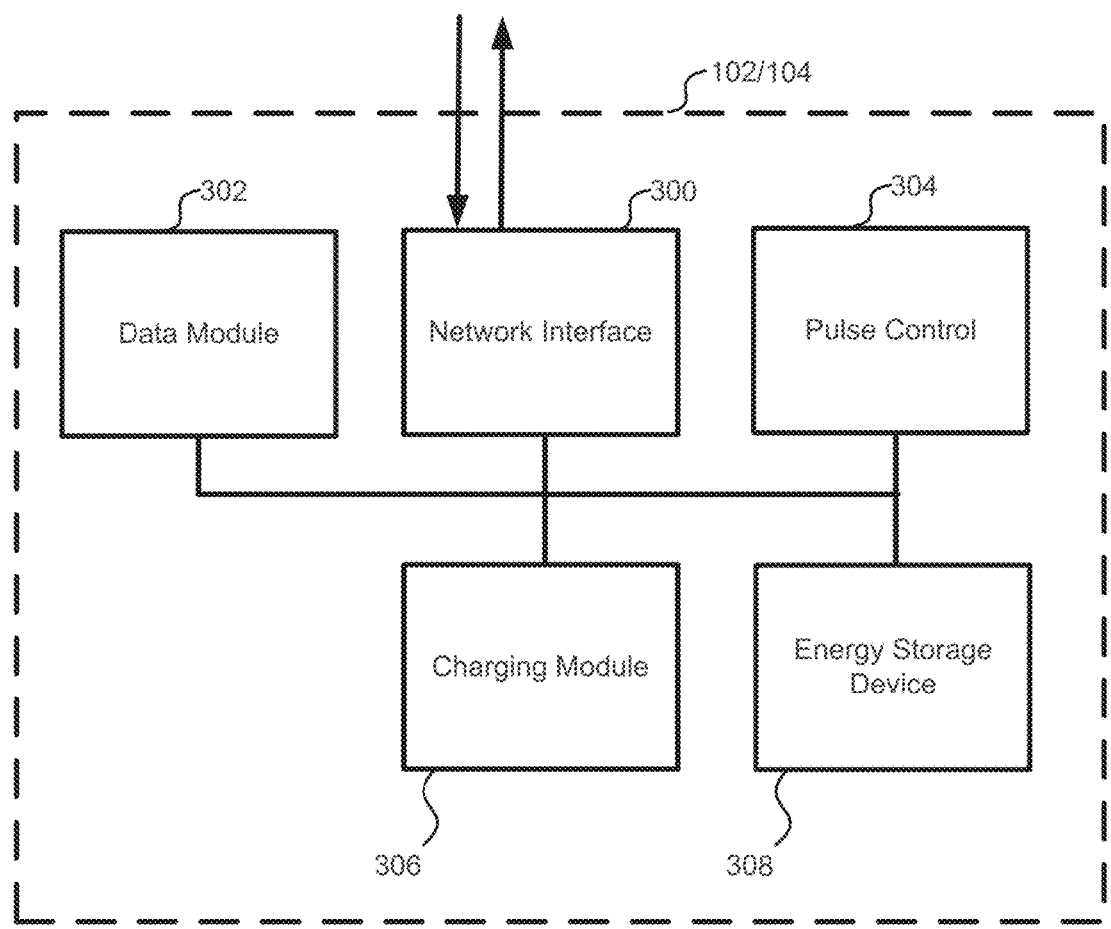
FIG. 3 is a schematic illustration of one embodiment of the architecture of the external pulse generator and/or of the implantable pulse generator that is a part of the implantable neurostimulation system.

With reference now to FIG. 3, a schematic illustration of one embodiment of the architecture of the external pulse generator 102 and/or of the implantable pulse generator 104 is shown. In some embodiments, each of the components of the architecture of the one of the pulse generators 102, 104 can be implemented using the processor, memory, and/or other hardware component of the one of the pulse generators 102, 104. In some embodiments, the components of the architecture of the one of the pulse generators 102, 104 can include software that interacts with the hardware of the one of the pulse generators 102, 104 to achieve a desired outcome.

In some embodiments, the pulse generator 102/104 can include, for example, a network interface 300, or alternatively, a communication module. The network interface 300, or alternatively, the communication module, can be configured to access the network 110 to allow communication between the pulse generator 102, 104 and the other components of the implantable neurostimulation system 100. In some embodiments, the network interface 300, or alternatively, a communication module, can include one or several antennas and software configured to control the one or several antennas to send information to and receive information from one or several of the other components of the implantable neurostimulation system 100.

The pulse generator 102, 104 can further include a data module 302. The data module 302 can be configured to manage data relating to the identity and properties of the pulse generator 102, 104. In some embodiments, the data module can include one or several databases that can, for example, include information relating to the pulse generator 102, 104 such as, for example, the identification of the pulse generator, one or several properties of the pulse generator 102, 104, or the like. In one embodiment, the data identifying the pulse generator 102, 104 can include, for example, a serial number of the pulse generator 102, 104 and/or other identifier of the pulse generator 102, 104 including, for example, a unique identifier of the pulse generator 102, 104. In some embodiments, the information associated with the property of the pulse generator 102, 104 can include, for example, data identifying the function of the pulse generator 102, 104, data identifying the power consumption of the pulse generator 102, 104, data identifying the charge capacity of the pulse generator 102, 104 and/or power storage capacity of the pulse generator 102, 104, data identifying potential and/or maximum rates of charging of the pulse generator 102, 104, and/or the like.

The pulse generator 102, 104 can include a pulse control 304. In some embodiments, the pulse control 304 can be configured to control the generation of one or several pulses by the pulse generator 102, 104. In some embodiments, for example, this information can identify one or several pulse patterns, programs, or the like. This information can further specify, for example, the frequency of pulses generated by the pulse generator 102, 104, the duration of pulses generated by the pulse generator 102, 104, the strength and/or magnitude of pulses generated by the pulse generator 102, 104, or any other details relating to the creation of one or several pulses by the pulse generator 102, 104. In some embodiments, this information can specify aspects of a pulse pattern and/or pulse program, such as, for example, the duration of the pulse pattern and/or pulse program, and/or the like. In some embodiments, information relating to and/or for controlling the pulse generation of the pulse generator 102, 104 can be stored within the memory.

The pulse generator 102, 104 can include a charging module 306. In some embodiments, the charging module 306 can be configured to control and/or monitor the charging/recharging of the pulse generator 102, 104. In some embodiments, for example, the charging module 306 can include one or several features configured to receive energy for recharging the pulse generator 102, 104 such as, for example, one or several inductive coils/features that can interact with one or several inductive coils/features of the charger 116 to create an inductive coupling to thereby recharge the pulse generator 102, 104.

In some embodiments, the charging module 306 can include hardware and/or software configured to monitor the charging of the pulse generator 102, 104. In some embodiments, the hardware can include, for example, a charging coil configured to magnetically couple with a charging coil of the charger 116. In some embodiments, these features can be configured to monitor the temperature of one or several components of the pulse generator 102, 104, the rate of charge of the pulse generator 102, 104, the charge state of the pulse generator 102, 104, or the like. These features can include, for example, one or several resistors, thermistors, thermocouples, temperature sensors, current sensors, charge sensors, or the like. In some embodiments, the charging module 306 can be configured to monitor, for example, voltage of the energy storage features, current flowing through, for example, a shunt circuit configured to channel excess current, one or several temperatures of, for example, the energy storage features and/or of the pulse generator 102, 104, the presence of a detectable charge field, the charge state of the energy storage features, and/or the like. In some embodiments, the one or several parameters can be provided to the network interface 300, and communicated via network 114 to other components of the implantable neurostimulation system 100.

The pulse generator 102, 104 can include an energy storage device 308. The energy storage device 308, which can include the energy storage features, can be any device configured to store energy and can include, for example, one or several batteries, capacitors, fuel cells, or the like. In some embodiments, the energy storage device 308 can be configured to receive charging energy from the charging module 306.

Figure 4:
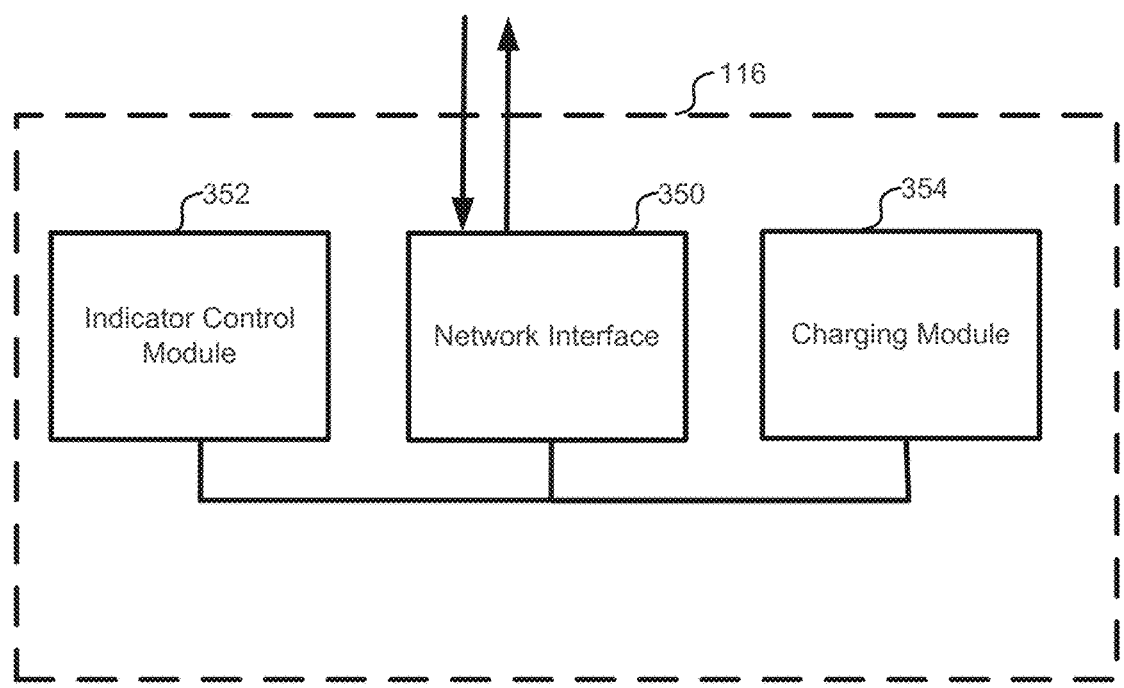
FIG. 4 is a schematic illustration of one embodiment of the charger that is a part of the implantable neurostimulation system.

With reference now to FIG. 4, a schematic illustration of one embodiment of the charger 116 is shown. In some embodiments, each of the components of the architecture of the charger 116 can be implemented using the processor, memory, and/or other hardware component of the charger 116. In some embodiments, the components of the architecture of the charger 116 can include software that interacts with the hardware of the charger 116 to achieve a desired outcome.

In some embodiments, the charger 116 can include, for example, a network interface 350, or alternatively, a communication module. The network interface 350, or alternatively, a communication module, can be configured to access the network 110 to allow communication between the charger 116 and the other components of the implantable neurostimulation system 100. In some embodiments, the network interface 350, or alternatively, a communication module, can include one or several antennas and software configured to control the one or several antennas to send information to and receive information from one or several of the other components of the implantable neurostimulation system 100.

In some embodiments, the charger 116 can include an indicator control module 352. In some embodiments, the indicator control module 352 can be configured to receive data relating to one or several parameters measured at the implantable pulse generator 104. The indicator control module 352 can use this information to determine whether charging would be improved by repositioning and/or reorienting of the charger 116 with respect to the implantable pulse generator 104. In some embodiments, this determination can include determining the relative effectiveness of the charging at a second, current position as compared to a first, previous position, and controlling the indicator to indicate increased charging effectiveness if the charging is more effective at the second position than and the first position, or similarly controlling the indicator to indicate the decreased charging effectiveness if the charging is less effective at the second position than at the first position. In some embodiments, this can include comparing the data received from the implantable pulse generator 104 to stored data to determine whether the charging effectiveness of the current position of the charger 116 is sufficient or insufficient. In the event that the charging effectiveness is insufficient, then the indicator control module 352 can be configured to control the indicator to indicate this insufficiency of the charging effectiveness. Similarly, in the event that the charging effectiveness is sufficient, then the indicator control module 352 can be configured to control the indicator to indicate this sufficiency of the charging effectiveness.

The charger 116 can include a charging module 354. The charging module 354 can be configured to control and/or monitor the charging of one or several of the pulse generators 102, 104. In some embodiments, for example, the charging module 354 can include one or several protocols that can request information from the one or several pulse generators 102, 104 at one or several times before, during, and after charging. This information can be received by the charger 116 from the pulse generator 102, 104 and can be used to control the generation of and/or properties of the charge field. In some embodiments, the charging module 354 can include one or several features configured to transmit energy charging coils that can magnetically couple with the charging coil of the pulse generator 102, 104 to thereby recharge the pulse generator 102, 104.

In some embodiments, the charging module 354 can be configured to power the charging coil of the charger 116 at any desired power level across a continuous power spectrum, and in some embodiments, the charging module 354 can be configured to power the charging coil of the charger 116 at one of several discrete power levels across a digitized power spectrum. In one such embodiment, for example, the charging module can be configured to power the charging coil of the charger 116 at one of 3, 4, 5, 6, 7, 8, 9, 10, 15, 20, 30, 50, 100, or any other or intermediate discrete power levels.

Figure 5:
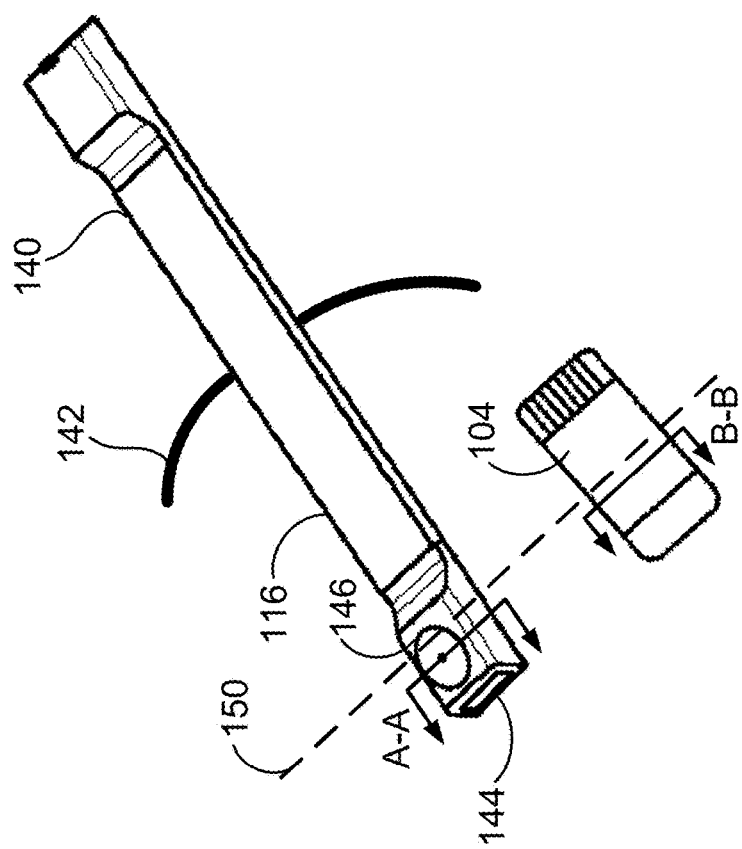
FIG. 5 is a perspective view of one embodiment of an implantable pulse generator and a charger.

With reference now to FIG. 5, a perspective view of one embodiment of the implantable pulse generator 104 and the charger 116 is shown. The charger 116 includes an elongate body 140. The elongate body 140 can be configured to be placed against the body of the patient such as, for example, directly against the skin of the patient, and/or proximate to the skin of the patient such as, for example, against a piece of clothing or apparel worn by the patient.

In some embodiments, the charger 116 can include at least one retention feature 142 that can be configured to hold the elongate body 140 in a desired position against the patient's body. In some embodiments, the retention feature 142 can be, for example, a strap, a band, or the like. In one such embodiment, for example, in which the charger 116 is placed on a portion of the body, such as, for example, the neck, torso, or limb, including, one of a leg, a foot, an arm, and a hand, the retention feature 142 can secure the charger 116 to that portion of the body and can secure the position and orientation of the charger 116 with respect to that portion of the body. In some embodiments, the retention feature 142 can be configured to hold the elongate body 140 of the charger 116 in a constant orientation with respect to the body of the patient. In some embodiments, a constant orientation may include some variations of the orientation of the elongate body 140 described by an angle measured from a longitudinal axis of the elongate body 140 in a first position to the longitudinal axis of the elongate body 140 in a second position. In some embodiments, this angle can be, for example, 1 degree, 5 degrees, 10 degrees, 15 degrees, 20 degrees, 30 degrees, 40 degrees, or any other or intermediate angle.

The charger 116 can include a charge head 144. The charge head 144 can include one or several features to facilitate the charging of the implantable pulse generator 104. In some embodiments, these features can include, for example, the charge head charging coil that will be discussed at greater length below.

As seen in FIG. 5, the charge head 144 includes a rotatable mount 146. In some embodiments, the rotatable mount 146 can be connected to the charging coil of the charge head 144 and can be configured to allow the rotation of the charging coil. The rotatable mount can include one or several features that can facilitate the rotation/re-orientation of the rotatable mount. These can include, for example, a feature configured to engage with, for example, a key, a screwdriver, a wrench, or the like, one or several features configured to facilitate digital manipulation such as, for example, one or several knurls, grips, or the like, or any other feature. In some embodiments, for example, the rotatable mount 146 can be configured to allow the manipulation of the angular position of the charge head charging coil with respect to, for example, the longitudinal axis of the elongate member 140.

As further seen in FIG. 5, the implantable pulse generator 104 can be positioned with respect to the charger 116 to allow recharging of the implantable pulse generator 104. In some embodiments, the implantable pulse generator 104 can be positioned so as to be within an effective distance or range from the charger 116. In some embodiments, this distance can be such that recharging of the implantable pulse generator 104 is effective, and the distance can be, for example, within 10 cm of the charge head 144, 5 cm of the charge head 144, 4 cm of the charge head 144, 3 cm of the charge head 144, 2 cm of the charge head 144, 1 cm of the charge head 144, 0.5 cm of the charge head 144, 0.1 cm of the charge head 144, and/or any other or intermediate distance from the charge head 144. In some embodiments, the implantable pulse generator 104 can be positioned such that the implantable pulse generator 104 is directly below the charge head 144 of the charger 116. This positioning is indicated in FIG. 5 by axis 150. Alternatively, in some embodiments, implantable pulse generator 104 can be positioned so as to not be directly below the charge head 144 of charger 116.

Figure 6:
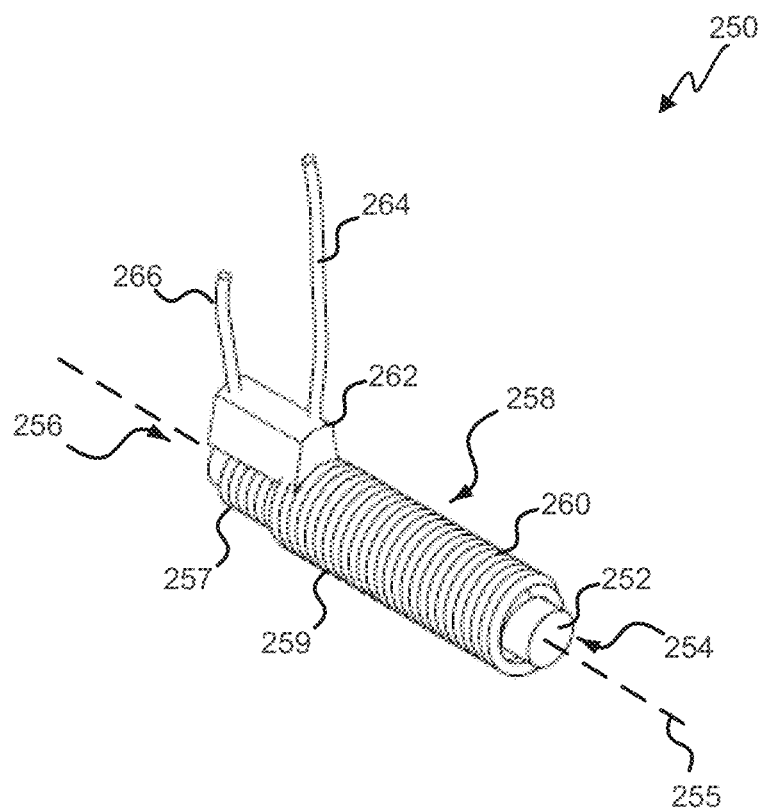
FIG. 6 is a perspective view of one embodiment of a charging coil that can be used in an implantable pulse generator.

With reference now to FIG. 6, a perspective view of one embodiment of a receiving coil 250, which can be any charging coil including, for example, a charging coil that transmits or receives energy, that can be used in the implantable pulse generator 104 is shown. The receiving coil 250 can comprise a variety of shapes and sizes and can be made of a variety of materials. The charging coil can comprise a solenoid. In some embodiments, the receiving coil 250 can be sized and shaped so as to fit within the implantable pulse generator 104, and specifically inside of a housing of the implantable pulse generator 104. In one embodiment, for example, the charging coil can be positioned proximate to a surface of the housing such that no other components of the implantable pulse generator 104 are between the receiving coil 250 and this surface. In some embodiments, the implantable pulse generator 104 can be implanted such that this surface is proximate to the skin of the patient and/or relatively more proximate to the skin of the patient than other portions of the implantable pulse generator.

In some embodiments, the receiving coil 250 can be configured to magnetically couple with features of the charger 116 such as, for example, a charging coil of the charger 116 to recharge the one or several energy storage features of the implantable pulse generator 104.

In some embodiments, and to facilitate the magnetic coupling of the receiving coil 250 with the charging coil of the charger 116, the receiving coil 250 of the implantable pulse generator 104 can have a high Q factor. In some embodiments, a high Q factor can have a Q value of at least 10, 20, 30, 40, 50, 75, 100, 150, 200, 300 and/or any other or intermediate value. In some embodiments, for example, the Q factor of the receiving coil 250 can be, for example, at least 10, at least 20, at least 30, at least 40, at least 50, at least 60, at least 70, at least 80, at least 100, at least 120, at least 200, and/or any other or intermediate value.

The receiving coil 250 can include a core 252. The core 252 can comprise a variety of shapes and sizes and can be made from a variety of materials. In some embodiments, the core 252 can be sized and shaped to facilitate the wrapping of one or several wires around the core 252 and/or the core 252 can be sized and shaped to achieve and/or facilitate in achieving a desired Q factor for the receiving coil 250. In some embodiments, the core 252 can comprise a ferritic core, and in some embodiments, the core 252 can comprise a soft ferritic core.

In some embodiments, and as shown in FIG. 6, the core 252 can comprise an elongate member, and can specifically comprise an elongate cylindrical member that can have, a distal, first end 254 and a proximal, second end 256. As seem in FIG. 6, an axis 255, which can be a longitudinal axis, can extend along the centerline of the core 252 between the first end 254 and the second end 256, and the length of the core 252 can be measured and/or defined with respect to this axis 255. In some embodiments, the length of the core 252 can be, for example, approximately 0.1 inches, 0.2 inches, 0.3 inches, 0.4 inches, 0.5 inches, 0.6 inches, 0.7 inches, 0.8 inches, 0.9 inches, 1 inch, 1.5 inches, 2 inches, 5 inches, and/or any other or intermediate length. In some embodiments, the core can have a radius, measured from the axis 255 of approximately 0.01 inches, 0.02 inches, 0.03 inches, 0.04 inches, 0.05 inches, 0.06 inches, 0.07 inches, 0.08 inches, 0.09 inches, 0.098 inches, 0.1 inches, 0.15 inches, 0.2 inches, 0.5 inches, and/or any other or intermediate radius.

The receiving coil 250 can further include a plurality of windings 258 around the core 252. The windings 258 can, together with the core 252, allow receiving coil 250 to magnetically couple with charger 116 to recharge the energy storage features of the implantable pulse generator 104. In some embodiments, the windings 258 can be made by looping wire 260, which wire 260 can be any type of wire including, for example, a litz wire, and which can be any material having desired properties, and specifically can be a metal wire, one or more times around core 252. In some embodiments, the windings 258 can comprise any desired number of loops of wire, and can, for example, comprise 2 loops, 5 loops, 10 loops, 15 loops, 20 loops, 25 loops, 29 loops, 30 loops, 35 loops, 40 loops, 50 loops 100 loops, 200 loops, 1,000 loops, and/or any other or intermediate number of loops.

In some embodiments, and as depicted in FIG. 6, the wire 260 can be looped around core 252 so as to create a plurality of layers of loops at different radial distances from axis 255. As specifically depicted in FIG. 6, a first layer of loops 257 is positioned so as to contact core 252 and to be a first radial distance from axis 255, and a second layer of loops 259 is positioned so as to contact the first layer of loops 257 and be a second radial distance from axis 255. In some embodiments, the first layer of loops 257 can comprise 1 loop, 2 loops, 5 loops, 10 loops, 12 loops, 13 loops, 15 loops, 16 loops, 18 loops, 20 loops, 30 loops, 50 loops, 100 loops, and/or any other or intermediate number of loops, and the second layer of loops 259 can comprise 1 loop, 2 loops, 5 loops, 10 loops, 12 loops, 13 loops, 15 loops, 16 loops, 18 loops, 20 loops, 30 loops, 50 loops, 100 loops, and/or any other or intermediate number of loops. In the embodiment depicted in FIG. 6, the first radial distance is less than the second radial distance, and thus the radius of the loops of the first layer of loops 257 is less than the radius of the loops of the second layer of loops 259.

The receiving coil 250 can include a capacitor 262. The capacitor 262 can comprise a variety of shapes and sizes and can have a variety of electrical properties. In some embodiments, for example, the capacitor 262 can comprise a high Q capacitor and in some embodiments, can be a high Q COG capacitor.

The capacitor 262 can, in connection with windings 258, create a tank circuit. In some embodiments, this tank circuit can be a high Q tank circuit. In some embodiments, the high Q tank circuit can have a Q value of at least 10, 20, 30, 40, 50, 75, 100, 150, 200, 300, and/or any other or intermediate value. The tank circuit can increase the Q factor of the receiving coil 250. This Q factor of the receiving coil 250 increases as the distance between the windings 258 and the capacitor 262 decreases. Thus, in some embodiments, the capacitor can, and as shown in FIG. 6, be placed on the windings 258, and in some embodiments, the capacitor 262 can be placed in proximity to the windings 258 such as, for example, a distance of less than 5 cm from the windings 258, less than 4 cm from the windings 258, less than 3 cm from the windings 258, less than 2 cm from the windings 258, less than 1 cm from the windings 258, less than 0.5 cm from the windings 258, less than 0.1 cm from the windings 258, and/or any other or intermediate distance from the windings 258.

The receiving coil 250 can include a first lead 264 and a second lead 266. The first and second leads 264, 266 can be used to electrically connect the receiving coil 250 to other features and/or components of the implantable pulse generator 104. In some embodiments, the leads 264, 266 can extend from the capacitor 262, and in some embodiments, the leads 264, 266 can extend from the windings 258.

Figure 7:
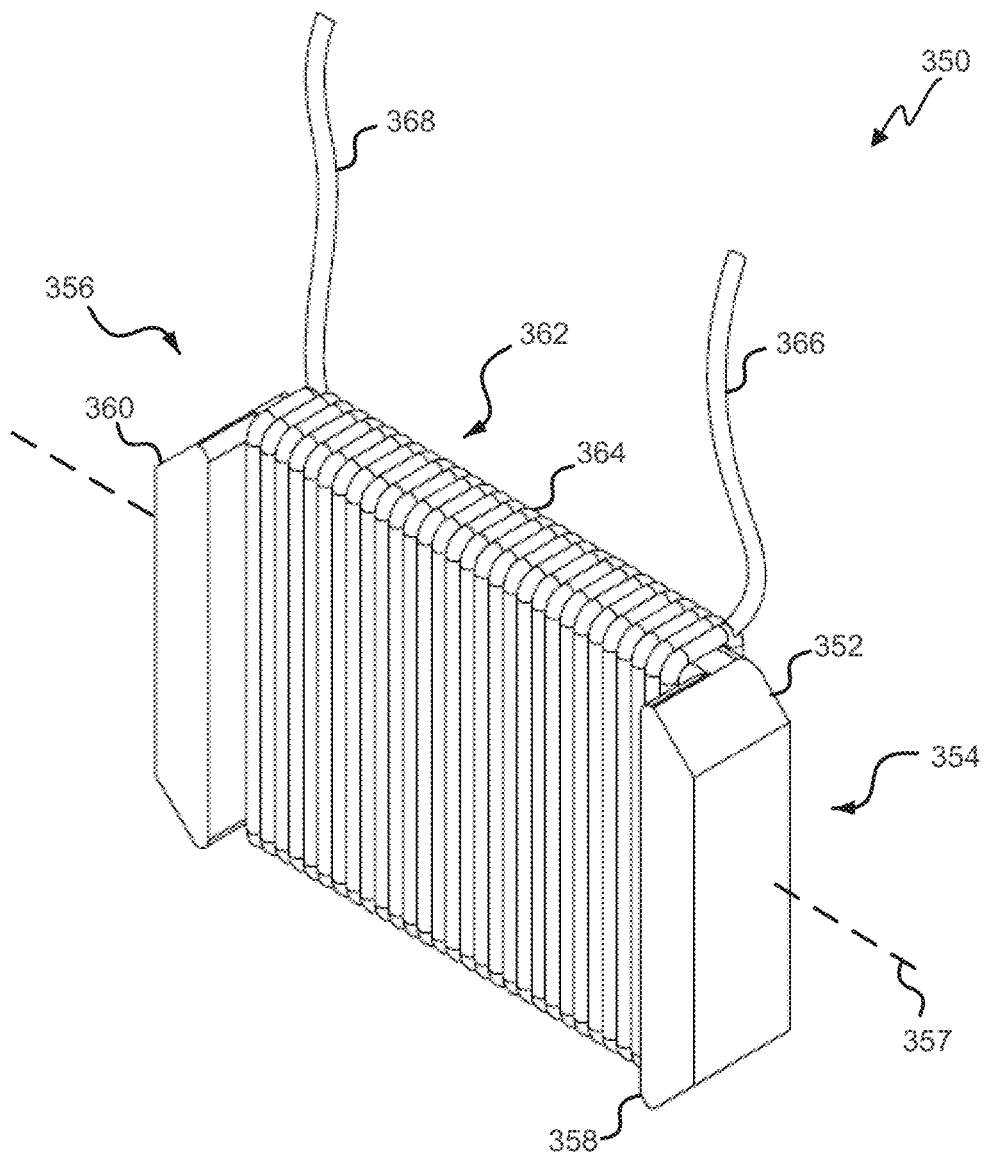
FIG. 7 is a perspective view of one embodiment of a charging coil that can be used in a charger.

With reference now to FIG. 7, a perspective view of one embodiment of a transmitting coil 350 that can be used in a charger is shown. The transmitting coil 350 can be any charging coil, including, for example, a charging coil that transmits or receives energy. The transmitting coil 350 can comprise a variety of shapes and sizes and can be made of a variety of materials. In some embodiments, the transmitting coil 350 can comprise a solenoid. In some embodiments, the transmitting coil 350 can be sized and shaped so as to fit within the charger 116, and specifically within the charge head 144 of the charger 116. In some embodiments, the transmitting coil 350 can be configured to magnetically couple with features of the implantable pulse generator 104 such as, for example, the receiving coil 250 of the implantable pulse generator 104 to recharge the one or several energy storage features of the implantable pulse generator 104.

In some embodiments, and to facilitate the magnetic coupling of the transmitting coil 350 with the receiving coil 250, the transmitting coil 350 can have a high Q factor. In some embodiments, for example, the Q factor of the transmitting coil 350 can be, for example, at least 50, at least 100, at least 150, at least 200, at least 250, at least 250, at least 350, at least 350, at least 450, at least 500, at least 1,000, and/or any other or intermediate value. In some embodiments, the Q value of the transmitting coil 350 can be any value that is larger than the Q value of the Q value of the receiving coil 250. In some embodiments, the Q value of the transmitting coil 350 can be, for example, 25, 50, 75, 100, 120, 150, 200, 220, 250, 300, 400, 500, 1,000, or any other or intermediate value larger than the Q value of the receiving coil 250.

The transmitting coil 350 can include a core 352. The core 352 can comprise a variety of shapes and sizes and can be made from a variety of materials. In some embodiments, the core 352 can be sized and shaped to facilitate the wrapping of one or several wires around the core 352 and/or the core 352 can be sized and shaped to achieve and/or facilitate in achieving a desired Q factor for the transmitting coil 350. In some embodiments, the core 352 can comprise a metal core and/or a ferritic core, and in some embodiments, the core 352 can comprise a soft ferritic core.

In some embodiments, and as shown in FIG. 7, the core 352 can comprise an elongate member, and can specifically comprise an elongate rectangular member that can have first end 354 and a second end 356. As seem in FIG. 7, an axis 357, which can be a longitudinal axis, can extend along the centerline of the core 352 between the first end 354 and the second end 356, and the length of the core 352 can be measured and/or defined with respect to this axis 357.

The core 352 can comprise a first foot 358 and/or a second foot 360. In some embodiments, the first foot 358 can be located at and/or proximate to the first end 354 and the second foot 360 can be located at and/or proximate to the second end 356. In some embodiments, the first and second feet 358, 360 extend away from the axis 357, and in some embodiments, the first and second feet 358, 360 extend in the same direction and to the same extent away from the axis 357. In some embodiments, the first and second feet 358, 360 can be configured for sliding engagement with other components of the charger 116, and specifically with other components of the charge head 144. The first and second feet 358, 360 can, in some embodiments, be made of the same material as the core 352, and in some embodiments, the feet 358, 360 can be made of a different material than the core 352.

In some embodiments, the extension of the feet 358, 360 away from the axis 357 of the core 352 can facilitate in guiding and shortening the magnetic field, which corresponds to the charging field, generated by the transmitting coil 350. In some embodiments, this can increase the directionality of the magnetic field and can increase the coupling coefficient between the charger 116 and the implantable pulse generator 104.

The transmitting coil 350 can further include a plurality of windings 362 around the core 352. The windings 362 can, together with the core 352 allow transmitting coil 350 to magnetically couple with implantable pulse generator 104 to recharge the energy storage features of the implantable pulse generator 104. In some embodiments, the windings 362 can be made by looping wire 364, which wire 364 can be any type of wire including, for example, a litz wire, and which can be any material having desired properties, and specifically can be a metal wire, one or more times around core 352. In some embodiments, the windings 362 can comprise any desired number of loops of wire, and can, for example, comprise 2 loops, 5 loops, 10 loops, 15 loops, 20 loops, 25 loops, 29 loops, 30 loops, 35 loops, 40 loops, 50 loops 100 loops, 200 loops, 1,000 loops, and/or any other or intermediate number of loops. In some embodiments, the windings 362 can be exposed, and in some embodiments, the windings 362 can be covered by, for example, tape such as a mylar tape.

In some embodiments, although not depicted in FIG. 7, the wire 364 can be looped around core 352 so as to create a plurality of layers of loops at different radial distances from axis 357. Specifically a first layer of loops can be positioned so as to contact core 352 and to be a first radial distance from axis 357, and a second layer of loops can be positioned so as to contact the first layer of loops and be a second radial distance from axis 357. In such an embodiment, the first radial distance can be less than the second radial distance, and thus the volume encompassed by the loops of the first layer of loops can be less than the volume encompassed by the loops of the second layer of loops.

The transmitting coil 350 can include a first lead 366 and a second lead 368. The first and second leads 366, 368 can be used to electrically connect the transmitting coil 350 to other features and/or components of the charger 116. In some embodiments, the leads 366, 368 can be the ends of wire 364, and in some embodiments, the leads 366, 368 can be connected to the ends of wire 364.

Figure 8:
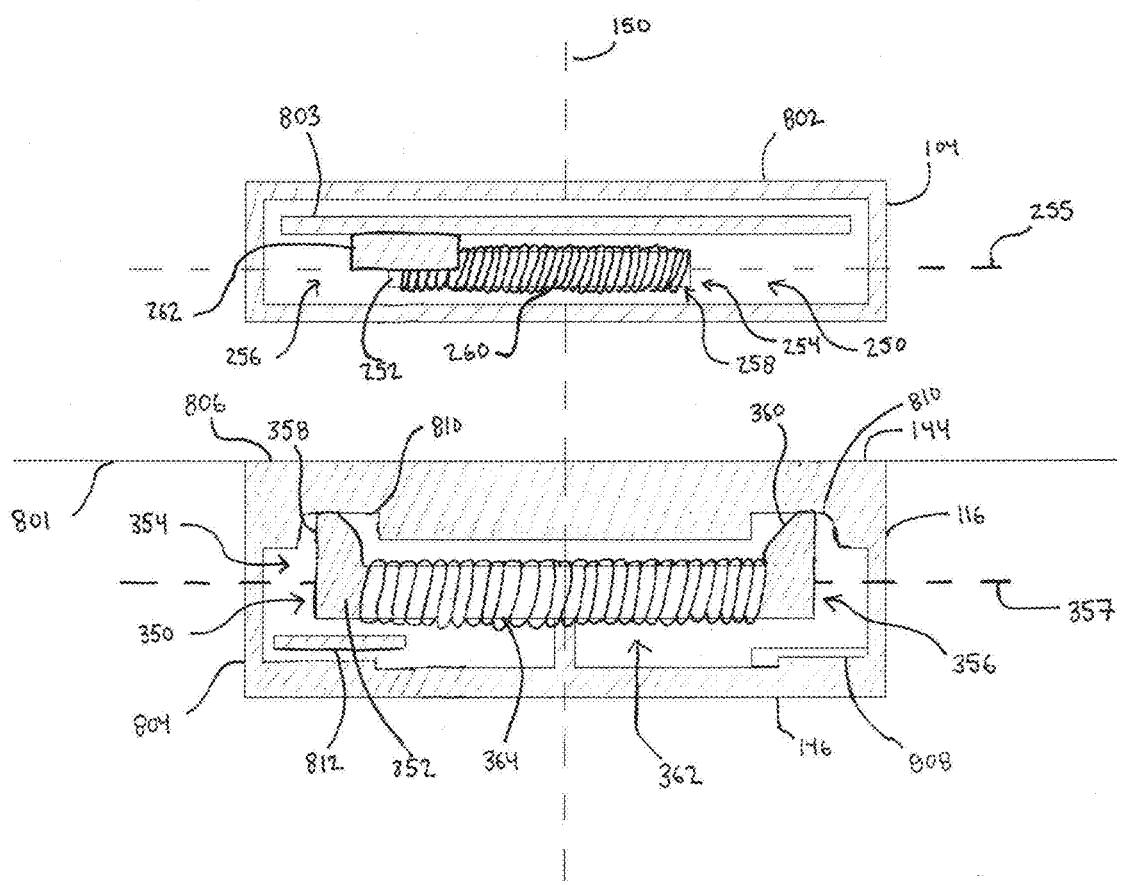
FIG. 8 is a section view of one embodiment of an implantable pulse generator and a charger.

With reference now to FIG. 8, a section view of one embodiment of the implantable pulse generator 104 and the charger 116 is shown. The section view is taken along the plane extending through A-A and B-B indicated in FIG. 2.

As seen in FIG. 5, the implantable pulse generator 104 includes a housing 802 that is sized, shaped, and configured to hold components of the implantable pulse generator 104 including, for example, the receiving coil 250. As depicted in FIG. 8, the receiving coil 250 includes the core 252 having the first end 254, the second end 256, and the axis 255 extending therebetween. The axis 255 shown in FIG. 8 is parallel with the plane of FIG. 8. The receiving coil 250 shown in FIG. 8 further includes windings 258 comprising loops of wire 260.

In some embodiments, the implantable pulse generator 104 can include circuitry 803. The circuitry 803 can include the processor, the energy storage features, one or several communication features, and the like. In some embodiments, this circuitry can be configured, to control the operation of the implantable pulse generator 104.

FIG. 8 further includes the charger 116, and specifically, the charge head 144 of the charger 116. The charger 116 includes a housing 804 that is sized, shaped, and configured to hold components of the charger 116 including, for example, the transmitting coil 350 and the rotatable mount 146. The housing 804 includes a base 806 that can be configured for placement adjacent to and/or on the patient's body, including on the patient's skin 801. In some embodiments, the base 806 can comprise a planar and/or substantially planar portion, referred to herein as a contact surface, that can be placed adjacent to and/or on the patient's body.

The housing 804 can further include a lock feature 808 that can secure the rotatable mount 146 in a desired position. The lock feature 808 can comprise a variety of shapes and sizes, and can be any desired feature or mechanism that can secure the rotatable mount in one or several desired locations. In some embodiments, the lock feature 808 can comprise one or several set-screws, latches, detents, or the like.

The rotatable mount 146 can be connected to the transmitting coil 350. In some embodiments, the connection of the rotatable mount 146 to the transmitting coil 350 can enable the changing of the orientation of the transmitting coil 350 with respect to the orientation of the longitudinal axis of the elongate member 140 by the rotation of the rotatable mount 146. In some embodiments, the rotatable mount 146 can be rotatable in one or two directions up to 20 degrees, up to 30 degrees, up to 45 degrees, up to 60 degrees, up to 90 degrees, up to 120 degrees, up to 180 degrees, up to 360 degrees, and/or any other or intermediate amount of rotation.

As shown in FIG. 8, the transmitting coil 350 can include the first and second ends 354, 356 and the axis 357 extending therebetween. The axis 357 shown in FIG. 8 is parallel with the plane containing FIG. 8.

The transmitting coil 350 can further include windings 362 comprising loops of wire 364. The transmitting coil 350 shown in FIG. 8 includes the first and second feet 358, 360 that extend from the axis 357 and are positioned within a track 810. In some embodiments, the track 810 can be located within a portion of the housing 804 and/or attached to the housing 804. The track 810 can be configured to receive the first and second feet 358, 360 and to facilitate in guiding the rotation of the transmitting coil 350 when the rotatable mount, and the therewith connected transmitting coil 350 is rotated. In some embodiments, the track 810 can be configured to allow rotations of the transmitting coil 350 in one or two directions up to 20 degrees, up to 30 degrees, up to 45 degrees, up to 60 degrees, up to 90 degrees, up to 120 degrees, up to 180 degrees, up to 360 degrees, and/or any other or intermediate amount of rotation.

The charger 116 can include circuitry 812. The circuitry 812 can include the processor, one or several communication features, and the like. In some embodiments, the circuitry 812 can be configured to receive one or several communications from the implantable pulse generator 104 and use information in these signals to detect the angular position of the receiving coil 250 with respect to the transmitting coil 350 of the charging head 146. In some embodiments, the detection of the angular position of the receiving coil 250 with respect to the transmitting coil 350 can include retrieving data relating to the power level of the charger, the effectiveness of the charging field at the implantable device 104, and data relating to changes in the effectiveness of the charging field at the implantable device 104 when the charger 116 is being moved relative to the implantable pulse generator 104, including, for example, when the angle between the receiving coil 250 and the transmitting coil 350 is changing. The angle between the receiving coil 250 and the charging coil 350 can then be determined based on this retrieved information. In some embodiments, this retrieved information can alternatively be used to look up one or more values stored within a database, which values can identify one or several potential angles between the receiving coil 250 and the charging coil 350. In some embodiments, this circuitry 812 can be configured, to control the operation of the charger 116.

As seen in FIG. 8, the axes 255, 357 are non-coaxial with each other. In contrast to better efficiency that results from the axial alignment of common implantable devices, the non-axial alignment of axes 255, 357 adversely affects the ability of the charging coils 250, 350 to magnetically couple. This ability to magnetically couple is further degraded to the extent that the axes 255, 357 of the charging coils 250, 350 are non-parallel. Thus, rotatable mount 146 can allow a user to re-orient the axes 255, 357 so that they are closer to parallel, and thereby improve the efficiency of the magnetic coupling between the charging coils 250, 350. Specifically, the embodiment shown in FIG. 8 allows the rotation of the transmitting coil 350 so that the axes 255, 357 of charging coils 250, 350 are parallel, or relatively more parallel.

With reference now to FIG. 8, a flowchart illustrating one embodiment of a process 500 for providing an alignment indicator for a charger 116 is shown. The process 500 can be performed by one or several of the components of the implantable neurostimulation system 100, and in some embodiments, can be performed by the charger 116. In some embodiments, the process 500 can be performed by some or all of the components of the charger 116 including, for example, the network interface 350, the indicator control module 352, and/or the charging module 354. The process 500 can be performed as part of recharging, and can be specifically performed to facilitate in the positioning and/or orienting of the charger 116 with respect to the implantable pulse generator 104. The process 500 can facilitate in positioning and/or orienting of the charger 116 through the control of one or several indicators which can provide information to the user regarding the effectiveness of a charging field at the implantable pulse generator 104, which effectiveness can vary, at least in part, based on the positioning and/or orienting of the charger 116 with respect to the implantable pulse generator 104.

The process 500 begins at block 502 wherein the charging coil of the charger 116 is operated at a first power level. In some embodiments, this first power level can describe the power of the charging field generated by the charging coil of the charger 116. This first power level can be obtained by controlling, for example, one or both of the voltage of the charging coil of the charger 116 and the current of the charging coil of the charger 116. In some embodiments, this first power level can be a zero power level, in which no charging field is generated, and in some embodiments, this first power level can be a non-zero power level, in which a charging field is generated. In some embodiments, the charging coil can be operated at the first level based on controls received from, for example, the charging module 354 of the charger 116.

After the charging coil is set to the first level, the process 500 proceeds to block 504, wherein a signal is received from a charged device. In some embodiments, the signal can be received via the network interface 350 of the charger 116. The signal can be received from the charged device, which can be the implantable pulse generator 104 via network 110, and specifically, can be received from the network interface 300 of the implantable pulse generator 104. In some embodiments, the signal can be analyzed by the processor of the charger 116. In some embodiments, the signal can be received at a discrete time, and in some embodiments, the signal can be repeatedly and/or continuously received during the performing of steps 506-514. In some such embodiments, process 500 can become a dynamic process in that many of steps 506-514 are simultaneously performed as the signal is repeatedly and/or continuously received.

The signal can include information relating to a parameter of the implantable pulse generator 104, and specifically to a parameter identifying the effect of the charging field on the implantable pulse generator 104. This parameter can, for example, identify the voltage induced by the charging field at the charging coil of the implantable pulse generator 104, identify the current induced by the charging field at the charging coil of the implantable pulse generator 104, identify a temperature of the implantable pulse generator 104, of a component of the implantable pulse generator 104, or of surrounding tissue, identify a charge state of the energy storage features of the implantable pulse generator 104, or the like.

After the signal received from the charged device has been received, the process 500 proceeds to block 506, wherein the signal is compared to one or several charging criteria. In some embodiments, these criteria can relate to whether and to what degree the charging field is charging the energy storage feature of the implantable pulse generator 104. These criteria can relate to, for example, whether the charging field is detectable at the implantable pulse generator 104, the voltage induced by the charging field in the charging coil of the implantable pulse generator 104, the current induced by the charging field in the charging coil of the implantable pulse generator 104, the charge state of the energy storage features of the implantable pulse generator 104, the temperature of the implantable pulse generator 104 or components thereof, or the like. In some embodiments, the comparison of the signal to the criteria can include a determination of whether the charging field allows safe charging of the implantable pulse generator 104 and the degree to which the charging field allows effective charging of the implantable pulse generator 104 such as, for example, whether the measured parameter (induced voltage, induced current, temperature, temp delta, etc. . . . falls within an acceptable range).

After the signal has been compared to the charging criteria, the process 500 proceeds to decision state 508, wherein it is determined if the charge coil level should be adjusted. In some embodiments, this can include, for example, increasing the level of the charging field if the charging field strength is inadequate, decreasing the level of the charging field if the charging field strength is too high, or the like. In some embodiments, this can further include determining that adjustment to the position and/or orientation of the charger 116 with respect to the implantable pulse generator 104 is desirable to increase the effectiveness of the charging field.

If it is determined that the coil level is to be adjusted, then the process 500 proceeds to block 510, wherein the coil level is adjusted. In some embodiments, this can include, for example, incrementing or decrementing the coil level to the next one of several discrete levels, or increasing the coil level by a predetermined value.

Returning again to decision state 508, if it is determined that the coil level should not be adjusted, then the process 500 proceeds to block 512, wherein the indicator, which can be an alignment indicator is activated. In some embodiments, in which the signal is repeatedly and/or continuously received, the indicator can be controlled to reflect the change of charging field effectiveness as represented by the signal over a period of time. Thus, in such an embodiment, if the effectiveness of the charging field increases, which can be due to, for example, the repositioning and/or reorienting of the charger 116, the indicator can be controlled to reflect this increased effectiveness. Similarly, if the effectiveness of the charging field decreases, which can be due to, for example, the repositioning and/or reorienting of the charger 116, the indicator can be controlled to reflect this decreased effectiveness.

Figure 9:
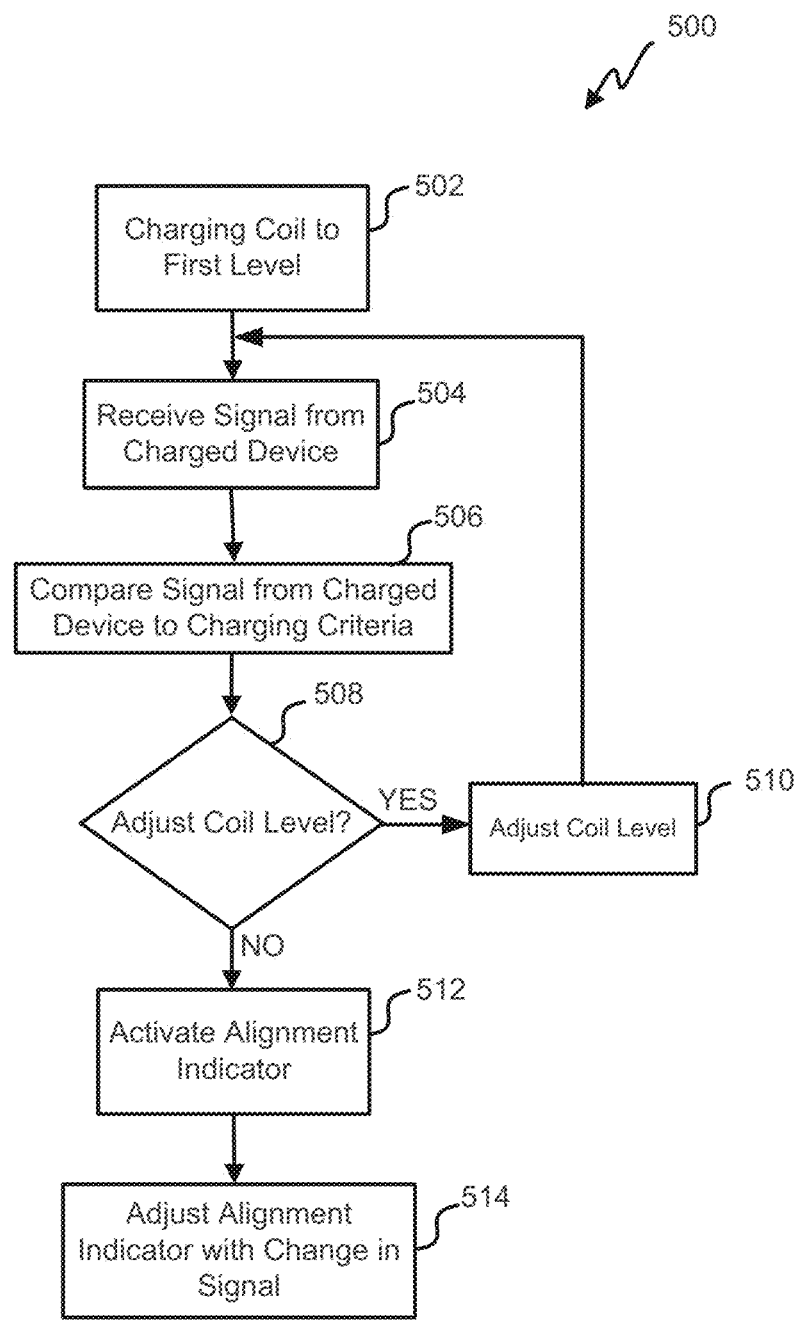
FIG. 9 is a flowchart illustrating one embodiment of a process for providing an alignment indicator for a charger.

With reference now to FIG. 9, a flowchart illustrating one embodiment of a process 600 for providing an alignment indicator for a charger based on detected variations in measured voltage and current is shown. The process 600 can be performed by one or several of the components of the implantable neurostimulation system 100, and in some embodiments, can be performed by the charger 116. In some embodiments, the process 600 can be performed by some or all of the components of the charger 116 including, for example, the network interface 350, the indicator control module 352, and/or the charging module 354. The process 600 can be performed as part of recharging, and can be specifically performed to facilitate in the positioning of the charger 116 with respect to the implantable pulse generator 104. The process 600 can facilitate in positioning of the charger 116 through the control of one or several indicators which can provide information to the user regarding the effectiveness of a charging field at the implantable pulse generator 104, which effectiveness can vary, at least in part, based on the positioning of the charger 116 with respect to the implantable pulse generator 104.

The process 600 begins at block 602 wherein the charger 116 is powered. In some embodiments, the powering of the charger 116 can correspond to a user turning the charger 116 on, or to selecting a charging mode of operation. After the charger is powered, the process 600 proceeds to block 604, wherein the charging coil is set to and/or operated at an initial level. In some embodiments, this initial level can describe the power of the charging field generated by the charging coil of the charger 116. This initial level can be obtained by controlling, for example, one or both of the voltage of the charging coil of the charger 116 and the current of the charging coil of the charger 116. In some embodiments, this initial level can be a zero power level, in which no charging field is generated, and in some embodiments, this initial level can be a non-zero power level, in which a charging field is generated. In some embodiments, the charging coil can be operated at the initial level based on controls received from, for example, the charging module 354 of the charger 116.

After the charging coil is set to an initial level, the process 600 proceeds to block 606, wherein communication between the implantable pulse generator 104 and the charger 116 is established. In some embodiments, this can include, for example, the charger 116 initiating communication by sending a query to the implantable pulse generator 104, and the implantable pulse generator 104 responding to the query of the charger 116.

After communication between the implantable pulse generator 104 and the charger 116 has been established, process 600 proceeds to decision state 608, wherein the communication link between the implantable pulse generator 104 and the charger is confirmed. If it is determined that communication has not been established, then the process 600 proceeds to block 610, wherein the event is logged in, for example, the memory of the charger, and the process 600 then proceeds to block 612, wherein the failure is indicated. In some embodiments, this indication can identify a specific failure, in this case, for example, a failure to establish communication between the implantable pulse generator 104 and the charger 116 is indicated, and in some embodiments, the indication of the failure can be generic.

Returning again to decision state 608, if it is determined that communication has been established, then the process 600 proceeds to block 614, wherein the indicators are activated. In some embodiments, this can include powering the indicators. After the indicators have been activated, the process 600 proceeds to block 616 wherein the coil level of the charging coil of the charger 116 is increased. After the coil level of the charging coil of the charger 116 has been increased, the process 600 proceeds to decision state 618, wherein it is determined if the charging coil is operating at its maximum level, and specifically if a preset upper limit has been reached. This determination can be made by identifying the present level of the charging coil and comparing the present level of the charging coil to the maximum possible level of the charging coil. If the present level of the charging coil is less than the maximum level of the charging coil, then the charging coil is not operating at its maximum level. Alternatively, if the present level of the charging coil is equal to the maximum level, then the charging coil is operating at the maximum level.

If it is determined that the charging coil is not operating at its maximum level, then the process 600 proceeds to decision state 620, wherein it is determined if the charging field is detected at the charged device, and specifically, if the charging field is detectable at the implantable pulse generator 104. In some embodiments, this determination can be made based on information that can be received, via a signal or via a communication from the implantable pulse generator 104. In some embodiments, this information can include data relating to one or several parameters, identifying the effect of the charging field on the implantable pulse generator 104. If it is determined, based on this data, that the charging field is not detectable at the charged device, then the process 600 returns to block 616, and proceeds as outlined above.

If it is determined that the charging field is detected at the charged device, then the process 600 proceeds to decision state 622, wherein it is determined if the charging field, as measured at the implantable pulse generator, is too strong, or alternatively, if the charging field is at an acceptable strength level. In some embodiments, an acceptable strength level can be a level at which the implantable pulse generator is capable of recharging the energy storage features. In some embodiments, this can be determined by comparing a current property of the energy storage features, such as, for example, the voltage of the energy storage features with a parameter of the charging field, such as, for example, the voltage induced by the charging field at the charging coil of the implantable pulse generator 104. In some embodiments, an acceptable strength level can be a level at which the implantable pulse generator is capable or recharging the energy storage features and an acceptable rate or within an acceptable time range.

In some embodiments, the acceptability of the strength level of the charging field can be determined by determining whether the charging field is causing excessive heating of the implantable pulse generator 104 or one or several components thereof, or if the strength of the charging field is resulting in the induction of undesirable current levels at the charging coil of the implantable pulse generator 104. In one embodiment, for example, this can be determined by measuring the current passing through the shunt circuit. In some embodiments, the shunt circuit can be any circuit that can dispose of or channel excess current generated by the charging field. If this current exceeds a threshold value, then the strength of the charging field may be too high. Similarly, if the temperature of the implantable pulse generator, or one or several components thereof exceeds a threshold temperature, then the strength of the charging field may be too high.

If it is determined that the charging field is too strong, then the process 600 proceeds to block 624, wherein the coil level is decreased. After the coil level has been decreased, the process 600 returns to decision state 622 and proceeds as outlined above.

Returning again to decision state 618, if it is determined that the charging coil has reached its maximum level, or returning again to decision state 622, if it is determined that the charging field is not too strong, then process 600 proceeds to decision state 626, wherein it is determined if the charging field is detected at the charged device, and specifically, if the charging field is detectable at the implantable pulse generator 104. In some embodiments, this decision state can replicate the determination of decision state 620. In such an embodiment, this determination can be made based on information that can be received, via a signal or via a communication from the implantable pulse generator 104. In some embodiments, this information can include data relating to one or several parameters, identifying the effect of the charging field on the implantable pulse generator 104. If it is determined, based on this data, that the charging field is not detected, then the process 600 proceeds to block 610 wherein the event is logged in, for example, the memory of the charger, and the process 600 then proceeds to block 612, wherein the failure is indicated. In some embodiments, this indication can identify a specific failure, in this case, for example, a failure create a charging field detectable at the implantable pulse generator 104 is indicated, and in some embodiments, the indication of the failure can be generic.

Returning again to decision state 626, if it is determined that the charging field is detected, then the process 600 proceeds to decision state 628 wherein it is determined if there is a change in the voltage induced by the charging field at the charging coil of the implantable pulse generator 104 The determination of decision state 628 can be based on data contained in one or several signals received from the implantable pulse generator 104 during the performance of the process 600.

In some embodiments, decision state 628 can, in connection with decision state 630 be used to determine whether the effectiveness of the charging field at the charging coil of the implantable pulse generator 104 is increasing or decreasing. In some embodiments, these changes to the effectiveness of the charge coil can be caused by the movement and/or repositioning and/or reorienting of the charger 116 with respect to the implantable pulse generator 104. In some embodiments the advancement of process 600 to decision state 628 can be delayed until a predetermined time interval has passed, and can be preceded by the activation of an indicator directing the user to reposition the charger 116. In such an embodiment, this can result in comparing the effectiveness of the charging field at a first time to the effectiveness of the charging field at a second time. In some embodiments, this can result in determining an effectiveness of the charging field at a first time based on a first signal, and determining the effectiveness of the charging field at a second time based on a second signal. In some embodiments, this can be repeated until a desired and/or maximum effectiveness level is identified, and in some embodiments, this can be repeated until a pre-determined amount of time has passed.

If it is determined that there is no change in the voltage induced by the charging field at the charging coil of the implantable pulse generator 104, then the process 600 proceeds to decisions state 630, wherein it is determined if there is a change in the current induced by the charging field at the charging coil of the implantable pulse generator 104. In some embodiments, this change in current induced by the charging field at the charging coil of the implantable pulse generator 104 can be based on data received at the charger 116 from the implantable pulse generator 104, which data can identify, for example, changes to the current flowing through the shunt circuit of the implantable pulse generator 104.

If it is determined that the current induced by the charging field at the charging coil of the implantable pulse generator 104 is higher at decisions state 630, as compared to the previous current induced by the charging field at the charging coil of the implantable pulse generator, or if it is determined that the voltage induced by the charging field at the charging coil of the implantable pulse generator 104 is higher at decision state 628, as compared to the previous voltage induced by the charging field at the charging coil of the implantable pulse generator, then the process 600 proceeds to block 632, wherein the indicators are controlled to indicate the increased voltage or current. In some embodiments, this can likewise indicate an increased effectiveness of the charging field at the charging coil of the implantable pulse generator 104.

Returning again to decision state 630, if it is determined that the current induced by the charging field at the charging coil of the implantable pulse generator 104 is lower at decisions state 530, as compared to the previous current induced by the charging field at the charging coil of the implantable pulse generator, or if it is determined that the voltage induced by the charging field at the charging coil of the implantable pulse generator 104 is lower at decision state 628, as compared to the previous voltage induced by the charging field at the charging coil of the implantable pulse generator, then the process 600 proceeds to block 634, wherein the indicators are controlled to indicate the decreased voltage or current. In some embodiments, this can likewise indicate an decreased effectiveness of the charging field at the charging coil of the implantable pulse generator 104.

After the indicators have been adjusted as in either block 632 or block 634, or returning again to decision state 630, if it is determined that there has been no change in the current induced by the charging field, the process 600 proceeds to decision state 636, wherein it is determined whether to continue process 600. In some embodiments, this can include, for example, determining whether a predetermined amount of time has passed, after which the process 600 should be terminated. In some embodiments, decision state 636 can include determining whether the effectiveness of the charging field has reached a maximum value, or exceeded an effectiveness threshold. If it is determined that process 600 should not be continued, then process 600 proceeds to block 638 and terminates. If it is determined that process 600 should continue, process 600 returns to decision state 628 and proceeds as outlined above. In some embodiments, the process 600 can be performed and/or repeated at any desired rate. In some embodiments, for example, process 600 can be performed and/or repeated 1,000 times per second, 500 times per second, 200 times per second, 100 times per second, 50 times per second, 25 times per second, 10 times per second, 5 times per second, 2 times per second, 1 times per second, 30 times per minutes, 20 times per minute, 10 times per minute, 5 times per minute, 1 time per minute, 30 times per hour, 20 times per hour, 10 times per hour, 5 times per hour, 1 time per hour, and/or any other or intermediate rate.

Figure 10:
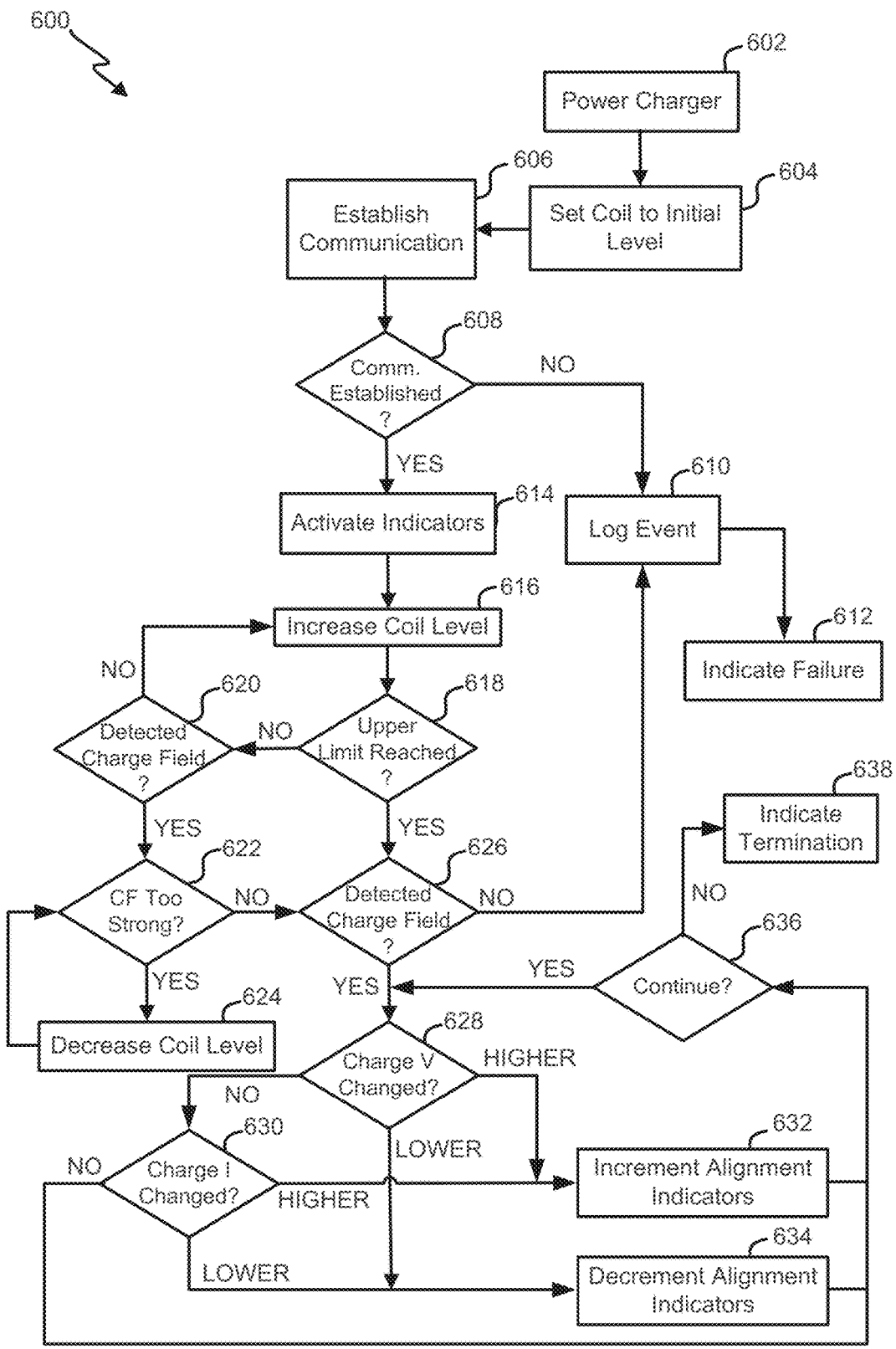
FIG. 10 is a flowchart illustrating one embodiment of a process for providing an alignment indicator for a charger based on detected variations in measured voltage and current.
Figure 11:
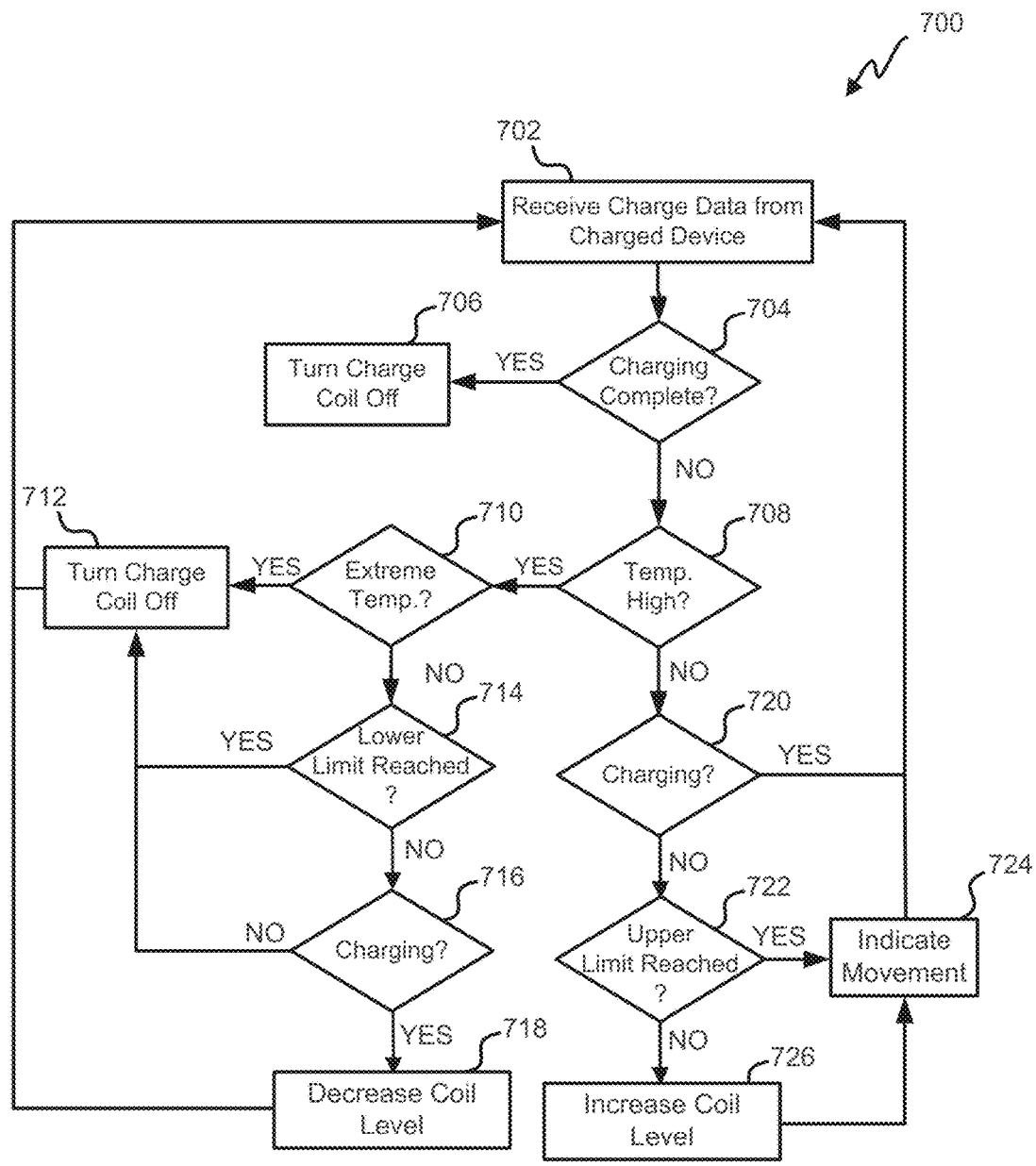
FIG. 11 is a flowchart illustrating one embodiment of a process in which movement of a charger is detected during the charging process.

With reference now to FIG. 10, a flowchart illustrating one embodiment of a process 700 in which movement of a charger is detected during the charging is shown. In some embodiments, the process 700 can be performed during the charging of the implantable pulse generator 104 to detect movement of the charger 116 with respect to the implantable pulse generator 104. The process can be performed by the implantable pulse generator 104, the charger 116, and/or any other components of the implantable neurostimulation system 100. The process 700 can be performed during the charging of the implantable pulse generator 104. In some embodiments, the process 700 can be continuously performed during the charging of the implantable pulse generator 104, and in some embodiments, the process 700 can be periodically performed during the charging of the implantable pulse generator.

The process 700 begins at block 702, wherein charge data is received by the charger 116 from a charged device, which can be, for example, the implantable pulse generator 104. In some embodiments, this charge data can include information identifying the charge state of the energy storage features of the implantable pulse generator 104, and in some embodiments, this information can identify whether the charging of the implantable pulse generator 104 is complete. This information can be received by the network interface 350 of the implantable pulse generator 104 from the network interface 300 of the implantable pulse generator 104.

After the charge data has been received, the process 700 proceeds to decision state 704, wherein it is determined if the charging of the implantable pulse generator 104 is complete. In some embodiments, this determination can be made based on the charge data received in block 702, which data can include information identifying the charge state of the energy storage features of the implantable pulse generator 104, and/or whether the charging of the implantable pulse generator 104 is complete. If it is determined that the charging is complete, then process 700 proceeds to bock 706, wherein the charging coil of the charger 116 is turned off.

Returning again to decision state 704, if it is determined that charging is not complete, process 700 proceeds to decision state 708, wherein temperature data contained in the received charge data is evaluated to determine if the temperature of the implantable pulse generator 104 or component thereof is too high. In some embodiments, the temperature data can identify the temperature of the implantable pulse generator 104 and/or of one or several components of the implantable pulse generator 104. The temperature data can be evaluated to determine whether the temperature of the implantable pulse generator 104, or of one or several components thereof, is too high. In some embodiments, this can include determining if the temperature of the implantable pulse generator 104 or of one or several components thereof is higher than a threshold value, which threshold value can be stored in memory of the implantable neurostimulation system 100. In some embodiments, the process 700 can, in decision state 708, determine if the temperature of the implantable pulse generator 104 or a component thereof is above a first threshold, which can be indicative of a temperature that is too high, but is at dangerous levels.

If it is determined that the temperature is too high, then the process 700 proceeds to decision state 710, wherein it is determined if the temperature of the implantable pulse generator 104 or component thereof is an extreme temperature. This determination can be based on temperature data received as part of the charge data in block 702.

In some embodiments, an extreme temperature can be a temperature at a dangerous level. In some embodiments, the difference between a temperature that is too high and an extreme temperature can be found in how each temperature is resolved. Thus, in some embodiments, a temperature that is too high may be resolved by decreasing the level of the charging field, whereas an extreme temperature is resolved by stopping charging.

If it is determined that the implantable pulse generator 104 or component thereof has reached an extreme temperature, then the process 700 proceeds to block 712, wherein the charging coil of the charger 116 is turned off. If it is determined that the implantable pulse generator 104 or component thereof has not reached an extreme temperature, then the process proceeds to decision state 714, wherein it is determined if the charging coil of the charger 116 is operating at its minimum level, which can be, for example, a preset lower limit. This determination can be made by identifying the present level of the charging coil and comparing the present level of the charging coil to the minimum possible level of the charging coil. If the present level of the charging coil is greater than the minimum level of the charging coil, then the charging coil is not operating at its minimum level. Alternatively, if the present level of the charging coil is equal to the minimum level, then the charging coil is operating at the minimum level.

If it is determined that the charging coil of the charger 116 is operating at its minimum level, then the process 700 proceeds to block 712, wherein the charging coil of the charger 116 is turned off. If it is determined that the charging coil of the charger 116 is not operating at its minimum level, then the process 700 proceeds to decision state 716, wherein it is determined if the implantable pulse generator 104 is charging. In some embodiments, this determination can comprise a binary determination of whether charging is occurring or not, and in some embodiments, this determination can comprise a qualification of the degree to which charging is occurring. In one specific embodiment, decision state 716 can include determining if charging is occurring and qualifying the degree to which charging is occurring. In this embodiment, decision state 716 can further include estimating the degree to which the coil level of the charging coil of the charger 116 can be decreased without ending charging and/or the degree to which a decrease in the coil level of the charging coil of the charger will impact the effectiveness of the charging field. If it is determined that the implantable pulse generator 104 is not charging, then the process 700 proceeds to block 712, wherein the charging coil of the charger 116 is turned off.

If it is determined that the implantable pulse generator 104 is charging, then the process 700 proceeds to block 718, wherein the level of the charging coil of the charger 116 is decreased. After the level of the charging coil of the charger 116 has been decreased, the process 700 proceeds to block 712, wherein the charging coil of the charger 116 is turned off.

Returning again to decision state 708, if it is determined that the temperature of the implantable pulse generator 104 or component thereof is not too high, then the process 700 proceeds to decision state 720, wherein it is determined if the implantable pulse generator 104 is charging. In some embodiments, this determination can comprise a binary determination of whether charging is occurring or not, and in some embodiments, this determination can comprise a qualification of the degree to which charging is occurring.

In some embodiments, the determination of decision state 720 can comprise a binary determination of whether charging is occurring or not, and in some embodiments, this determination can comprise a qualification of the degree to which charging is occurring. In one specific embodiment, decision state 716 can include determining if charging is occurring and qualifying the degree to which charging is occurring. In this embodiment, decision state 716 can further include estimating the degree to which the coil level of the charging coil of the charger 116 can be decreased without ending charging and/or the degree to which a decrease in the coil level of the charging coil of the charger will impact the effectiveness of the charging field.

If it is determined that the implantable pulse generator 104 is charging, then the process 700 returns to block 702 and proceeds as outlined above. In some embodiments, the return to block 702 can further include waiting a predetermined period of time before additional charge data is received, or before received charge data is analyzed.

If it is determined that the implantable pulse generator 104 is not charging, then the process 700 proceeds to decision state 722, wherein it is determined if the charging coil of the charger 116 is operating at its maximum level, which can be, for example, a preset upper limit. This determination can be made by identifying the present level of the charging coil and comparing the present level of the charging coil to the maximum possible level of the charging coil. If the present level of the charging coil is less than the maximum level of the charging coil, then the charging coil is not operating at its maximum level. Alternatively, if the present level of the charging coil is equal to the maximum level, then the charging coil is operating at the maximum level.

If it is determined that the charger 116 is operating at the maximum coil level, then process 700 proceeds to block 724, wherein the indicators are controlled to direct the user to reposition the charger 116 and/or to indicate the charger 116 has moved from its original position. After the indicators have been controlled, the process 700 can return to block 702 and proceed as outlined above. In some embodiments, and before returning to block 702, the process 700 proceeds to decision state 628 of process 600 in FIG. 9, and proceeds as outlined therein. In such an embodiment, after termination is indicated in block 638, process 700 would then return to block 702 and proceed as outlined above.

Returning now to decision state 722, if it is determined that the charge level of the charging coil of the charger 116 is not operating at a maximum level, the process 700 proceeds to block 726, wherein the coil level of the charging coil of the charger 116 is increased. After the coil level of the charging coil of the charger 116 has been increased, the process 700 proceeds to block 724 and continues as outlined above.

Figure 12:
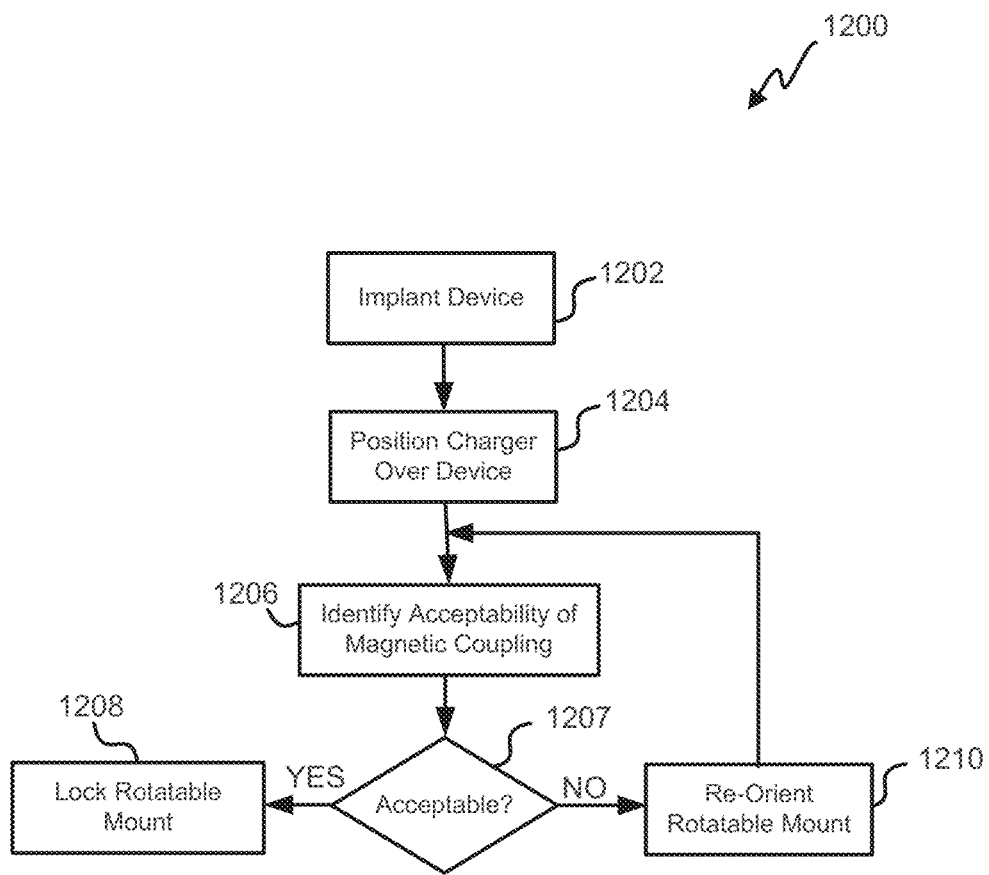
FIG. 12 is a flowchart illustrating one embodiment of a process for adjusting the rotatable mount of a charger.

With reference now to FIG. 12, a flowchart illustrating one embodiment of a process 1200 for adjusting the rotatable mount 146 of a charger 116 is shown. In some embodiments, this process 1200 can be performed by a component of one or both of the charger 116 and the implantable pulse generator 104, including, for example, the processor of one or both of the implantable pulse generator 104 and the charger 116.

The process 1200 begins in block 1202, wherein a device, such as the implantable pulse generator 104, is implanted. In some embodiments, this can include creating an incision in the skin, and a sub-dermal pocket for receiving the implantable pulse generator 104.

After the device has been implanted, the process 1200 proceeds to block 1204, wherein the charger 116 is positioned over, and/or proximate to the device, which device can include the implantable pulse generator 104. In some embodiments, this can include placing the charger 116 proximate to the implantable pulse generator 104. This can further include, for example, securing the charger 116 to the patient via the retention feature 142.

After the charger 116 has been placed proximate to the device, the process 1200 proceeds to block 1206, wherein the acceptability of the magnetic coupling is identified. In some embodiments, this can include the generation of a magnetic field of a first strength by the charger 116, the detection of the strength of the magnetic coupling at the implantable pulse generator 104, and the transmission of a signal indicating the strength of the magnetic coupling at the implantable pulse generator 104 to the charger 116. In some embodiments, this identification of the acceptability of the magnetic coupling can include determining a first orientation of the transmitting coil 350 with respect to the receiving coil 250, which can specifically include identifying the angle between the axis 255 of the receiving coil 250 and the axis 357 of the charge coil 350.

After the acceptability of the strength of the magnetic coupling has been identified, the process 1200 proceeds to decision state 1207, wherein it is determined if the strength of the magnetic coupling is acceptable. In some embodiments, the acceptability of the strength of the magnet coupling can be determined by compared the measured strength of the coupling to one or several thresholds. If the measured strength exceeds the threshold value, then the strength of the magnetic coupling can be acceptable. Conversely, if the measured strength does not exceed the threshold value, then the strength of the magnetic coupling can be unacceptable. In some embodiments, and as a part of decision state 1207, an indicator of a degree of acceptability and/or unacceptability can be provided to the user of the charger 116, which indicator can be a visual and/or audible indicator. In some embodiments, the indicator can be located in the charger 116, and in some embodiments, the indicator can be, for example, communicated to another device such as, for example, a smartphone, a tablet, a computer, or the like. In some embodiments, this can include, for example, an indication of the degree to which the rotatable mount 146 should be re-oriented, and direction in which the rotatable mount 146 should be re-oriented.

If it is determined that the strength of the magnetic coupling is acceptable, then the process 1200 proceeds to block 1208, wherein the rotatable mount is locked in place. In some embodiments, the rotatable mount 146 can be locked in place via the lock feature 808.

Returning again to decision state 1207, if it is determined that the strength of the magnetic coupling is unacceptable, then the process 1200 proceeds to block 1210, wherein the rotatable mount 146 is re-oriented, in other words, wherein the rotatable mount 146 and the thereto attached transmitting coil 350 are placed in a second orientation with respect to the receiving coil 250. In some embodiments, the re-orientation of the rotatable mount 146 can likewise re-orient the transmitting coil 350. In some embodiments, the angle between the axis 255 of the receiving coil 250 and the axis 357 of the transmitting coil 350 is smaller when the transmitting coil 350 is in than second orientation than when the charging coil is in the first, original orientation.

After the rotatable mount 146 has been re-oriented, the process 1200 returns to block 1206 and proceeds as outlined above. In some embodiments, through process 1200, the transmitting coil 350 can be oriented with respect to receiving coil 250 such that the axes 255, 357 of the charging coils 250, 350 are acceptably parallel such that the strength of the magnetic coupling between the charging coils 250, 350 exceeds the threshold of decision state 1207. Alternatively, in some embodiments, process 1200 can be repeated until the angle between axis 255 of receiving coil 250 and axis 357 of transmitting coil 350 is minimized.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of charging an implantable device, the method comprising:
    positioning a charging head comprising a transmitting coil attached to a retention feature proximate to an implantable device comprising a receiving coil;
    determining a first orientation of the transmitting coil with respect to the receiving coil; and
    rotating the attached transmitting coil until the transmitting coil has a second orientation with respect to the receiving coil, wherein the rotation of the transmitting coil is along a plane substantially parallel to a plane defined by the receiving coil.

2. The method of claim 1, wherein the transmitting coil has a longitudinal axis and at least one wire wrapped around the longitudinal axis.

3. The method of claim 2, wherein the receiving coil has a longitudinal axis and at least one wire wrapped around the longitudinal axis.

4. The method of claim 3, wherein determining the first orientation of the transmitting coil with respect to the receiving coil comprises determining an angle between the longitudinal axis of the transmitting coil with respect to the longitudinal axis of the receiving coil.

5. The method of claim 4, wherein the angle between the longitudinal axis of the transmitting coil is non-parallel with the longitudinal axis of the receiving coil in the first orientation.

6. The method of claim 4, wherein an angle between the longitudinal axis of the transmitting coil and the longitudinal axis of the receiving coil in the second orientation is less than the angle between the longitudinal axis of the transmitting coil and the longitudinal axis of the receiving coil in the first orientation, and wherein a charging efficiency in the first orientation is less than a charging efficiency in the second orientation.

7. The method of claim 3, wherein rotating the transmitting coil until the transmitting coil has a second orientation with respect to the receiving coil comprises determining when an angle between the longitudinal axis of the transmitting coil and the longitudinal axis of the receiving coil is minimized.

8. The method of claim 7, wherein the second orientation is reached when the angle between the longitudinal axis of the transmitting coil and the longitudinal axis of the receiving coil is minimized.

9. An implantable device comprising:
    a processor configured to control an operation of the implantable device and to generate a plurality of electrical impulses for stimulating a peripheral nerve of a patient;
    a lead configured for placement proximate to a peripheral nerve;
    an energy storage device configured to store energy; and
    a charging coil comprising:
        an elongate core having a first end, and second end, and a longitudinal axis extending therebetween; and
        a wire wrapped in a plurality of coils around the elongate core and the longitudinal axis of the elongate core;
    wherein the charging coil is attached to an outer surface of a body of the patient, the charging coil being rotatable with respect to a retention feature, wherein the charging coil is rotatable along a plane substantially parallel to a plane defined by the outer surface of the body of the patient.

10. The implantable device of claim 9, wherein the wire comprises litz wire.

11. The implantable device of claim 9, wherein the elongate core comprises a soft ferrite material.

12. The implantable device of claim 9, wherein the charging coil has a Q factor of at least 70.

13. The implantable device of claim 9, wherein the charging coil has a Q factor of at least 80.

14. The implantable device of claim 9, wherein the charging coil further comprises a capacitor electrically connected to the wire.

15. The implantable device of 14, wherein the capacitor comprises a high Q COG capacitor.

16. The implantable device of 14, wherein the capacitor is located on the charging coil.

17. The implantable device of 14, wherein the capacitor is located proximate to the charging coil.

18. The implantable device of 14, wherein the capacitor is positioned so as to create a high Q tank circuit.

19. A charging system comprising:
an implantable device comprising:
a receiving coil having:
an elongate core having a first end, a second end, and a longitudinal axis extending therebetween; and
a wire wrapped in a plurality of coils around the elongate core and the longitudinal axis of the elongate core; and
a charging head comprising:
a transmitting coil having:
an elongate core having a first end, a second end, and a longitudinal axis extending therebetween; and
a wire wrapped in a plurality of coils around the elongate core and the longitudinal axis of the elongate core;
wherein the transmitting coil is attached to a retention feature configured to be placed proximate to the implantable device, the transmitting coil being rotatable with respect to the retention feature, wherein the transmitting coil is rotatable along a plane substantially parallel to a plane defined by the receiving coil.

20. The charging system of claim 19, wherein the receiving coil comprises a capacitor electrically connected to the wire of the receiving coil.

21. The charging system of claim 19, wherein the charging head comprises a rotatable mount.

22. The charging system of claim 21, wherein the transmitting coil is attached to the rotatable mount.

23. The charging system of claim 22, wherein the rotatable mount is rotatable between a first position and a second position.

24. The charging system of claim 23, wherein the rotatable mount is lockable in the first position and in the second position.

25. The charging system of claim 22, further comprising circuitry configured to detect an angular position of the receiving coil with respect to the transmitting coil.

26. The charging system of claim 25, wherein the circuitry configured to detect an angular position of the receiving coil with respect to the transmitting coil are in the charging head.

27. A method of charging an implantable device, the method comprising:
positioning an external charger on an outer surface of a person's body proximate an implanted electrical pulse generator, the external charger including a housing, a retention feature, and a charging coil, wherein the charging coil is rotatable with respect to the retention feature, the implanted electrical pulse generator including a charging coil;
fixing the position of the external charger on the outer surface of the person's body; and
while the external charger is fixed on the outer surface of the person's body, rotating the charging coil of the external charger to change an orientation of the charging coil of the external charger relative to the charging coil of the implanted electrical pulse generator, wherein the rotation of the charging coil is along a plane substantially parallel to a plane defined by the outer surface of the person's body.

28. The method of claim 27, wherein the implanted electrical pulse generator further comprises at least one electrode implanted proximate a peripheral nerve of the person.

* * * * *